United States Patent
Burke, Jr. et al.

(10) Patent No.: US 7,226,991 B1
(45) Date of Patent: Jun. 5, 2007

(54) PHENYLALANINE DERIVATIVES

(75) Inventors: Terrence R. Burke, Jr., Bethesda, MD (US); Yang Gao, Brandord, CT (US); Zhu-jun Yao, Shanghai (CN); Dajun Yang, Gaithersburg, MD (US)

(73) Assignees: United States of America, represented by the Secretary, Department of Health and Human Services, Washington, DC (US); Georgetown University, Washington, DC (US)

( * ) Notice: Subject to any disclaimer, the term of this patent is extended or adjusted under 35 U.S.C. 154(b) by 0 days.

(21) Appl. No.: 09/937,150

(22) PCT Filed: Mar. 23, 2000

(86) PCT No.: PCT/US00/08231

§ 371 (c)(1),
(2), (4) Date: Mar. 26, 2002

(87) PCT Pub. No.: WO00/56760

PCT Pub. Date: Sep. 28, 2000

Related U.S. Application Data

(60) Provisional application No. 60/126,047, filed on Mar. 23, 1999.

(51) Int. Cl.
*C07K 5/08* (2006.01)
(52) U.S. Cl. .................. 530/331; 530/327; 530/328; 530/329; 530/330; 514/14; 514/15; 514/16; 514/17; 514/18; 514/19
(58) Field of Classification Search .............. 530/331, 530/327, 328, 329, 330; 514/14–19
See application file for complete search history.

(56) References Cited

U.S. PATENT DOCUMENTS

| | | | | |
|---|---|---|---|---|
| 3,906,031 A | * | 9/1975 | Carpino et al. ............ 560/32 |
| 4,394,519 A | * | 7/1983 | Carpino et al. ............ 560/32 |
| 4,879,398 A | * | 11/1989 | Getman et al. ............ 556/413 |
| 5,182,263 A | * | 1/1993 | Danho et al. ............ 514/16 |
| 5,200,546 A | * | 4/1993 | Burke, Jr. et al. ........ 558/190 |
| 5,272,268 A | * | 12/1993 | Toyoda et al. ............ 544/137 |
| 5,296,608 A | * | 3/1994 | Danho et al. ............ 548/253 |
| 5,369,110 A | * | 11/1994 | Schmidlin et al. ........ 514/281 |
| 5,457,114 A | * | 10/1995 | Stuber et al. ............ 514/319 |
| 5,463,062 A | * | 10/1995 | Hemmerle et al. ........ 546/168 |
| 5,491,253 A | * | 2/1996 | Stuk et al. ............ 560/27 |
| 5,508,437 A | * | 4/1996 | Danho et al. ............ 548/545 |
| 5,525,733 A | * | 6/1996 | Novack et al. ............ 548/253 |
| 5,580,979 A | * | 12/1996 | Bachovchin ............ 540/509 |
| 5,587,372 A | * | 12/1996 | Aszodi et al. ............ 514/202 |
| 5,612,370 A | * | 3/1997 | Atwal ............ 514/456 |
| 5,616,776 A | * | 4/1997 | Stuk et al. ............ 560/27 |
| 5,627,283 A | * | 5/1997 | St uber et al. ............ 546/205 |
| 5,646,036 A | * | 7/1997 | Schwall et al. ............ 435/252.3 |
| 5,679,842 A | * | 10/1997 | Kleiner ............ 562/15 |
| 5,686,292 A | * | 11/1997 | Schwall et al. ........... 424/143.1 |
| 5,688,992 A | * | 11/1997 | Burke et al. ............ 560/82 |
| 5,698,731 A | * | 12/1997 | Bosetti et al. ............ 560/24 |
| 5,707,624 A | * | 1/1998 | Nickoloff et al. ........ 424/158.1 |
| 5,710,129 A | * | 1/1998 | Lynch et al. ............ 514/18 |
| 5,710,173 A | * | 1/1998 | Tang et al. ............ 514/447 |
| 5,712,395 A | * | 1/1998 | App et al. ............ 544/344 |
| 5,753,687 A | * | 5/1998 | Mjalli et al. ............ 514/396 |
| 5,756,817 A | * | 5/1998 | Choi et al. ............ 560/115 |
| 5,773,411 A | * | 6/1998 | Wells et al. ............ 514/11 |
| 5,780,496 A | * | 7/1998 | Tang et al. ............ 514/414 |
| 5,786,454 A | * | 7/1998 | Waksman et al. ........... 530/402 |
| 5,789,427 A | * | 8/1998 | Chen et al. ............ 514/352 |
| 5,792,771 A | * | 8/1998 | App et al. ............ 514/266.3 |
| 5,792,783 A | * | 8/1998 | Tang et al. ............ 514/397 |
| 5,824,862 A | * | 10/1998 | Hiyoshi et al. ............ 426/438 |
| 5,834,504 A | * | 11/1998 | Tang et al. ............ 514/418 |
| 5,843,997 A | * | 12/1998 | Heinz et al. ............ 514/561 |
| 5,849,510 A | * | 12/1998 | Al-Obeidi et al. ............ 435/13 |
| 5,849,693 A | * | 12/1998 | Wells et al. ............ 514/11 |
| 5,849,742 A | * | 12/1998 | App et al. ............ 514/249 |
| 5,880,141 A | * | 3/1999 | Tang et al. ............ 514/339 |
| 5,883,110 A | * | 3/1999 | Tang et al. ............ 514/342 |
| 5,883,113 A | * | 3/1999 | Tang et al. ............ 514/418 |
| 5,883,116 A | * | 3/1999 | Tang et al. ............ 514/418 |
| 5,886,020 A | * | 3/1999 | Tang et al. ............ 514/418 |
| 5,886,195 A | * | 3/1999 | Tang et al. ............ 549/75 |
| 5,891,917 A | * | 4/1999 | Tang et al. ............ 514/604 |
| 5,912,183 A | * | 6/1999 | Comoglio et al. ........... 436/501 |
| 5,922,697 A | * | 7/1999 | Lunney et al. ............ 514/119 |
| 5,935,993 A | * | 8/1999 | Tang et al. ............ 514/445 |
| 5,948,658 A | * | 9/1999 | Landry ............ 435/188.5 |
| 5,958,957 A | * | 9/1999 | Andersen et al. ........... 514/364 |
| 5,965,558 A | * | 10/1999 | Mjalli et al. ............ 514/249 |

(Continued)

FOREIGN PATENT DOCUMENTS

WO    WO 94/07913    4/1994

(Continued)

OTHER PUBLICATIONS

Viallet (Lung Cancer 15 (3) 367-73, 1996).*

(Continued)

*Primary Examiner*—David Lukton
(74) *Attorney, Agent, or Firm*—Leydig, Voit & Mayer, Ltd

(57) ABSTRACT

Disclosed herein are phenylalanine derivative compounds of the following formula

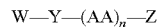

wherein Y is a phenylalanyl radical, AA is an amino acid, n is an integer of 1 to 15, and substituent variables W and Z are as described herein. The compounds can be used to inhibit SH2 binding with phosphoproteins, and to inhibit proliferation of tumor cells.

49 Claims, 17 Drawing Sheets

U.S. PATENT DOCUMENTS

| | | | | |
|---|---|---|---|---|
| 5,972,978 | A | * | 10/1999 | Andersen et al. ............ 514/361 |
| 5,981,569 | A | * | 11/1999 | App et al. .................... 514/419 |
| 5,981,755 | A | * | 11/1999 | Horwell et al. ........... 546/277.4 |
| 6,022,696 | A | * | 2/2000 | Harding et al. ............. 435/7.21 |
| 6,037,134 | A | * | 3/2000 | Margolis .................... 435/7.23 |
| 6,228,986 | B1 | * | 5/2001 | Lanter et al. ................ 530/317 |
| 6,307,090 | B1 | * | 10/2001 | Burke et al. ................... 560/76 |
| 6,410,585 | B1 | * | 6/2002 | Larsen et al. ................ 514/424 |

FOREIGN PATENT DOCUMENTS

| | | |
|---|---|---|
| WO | WO 95/11917 | 5/1995 |
| WO | WO 96/23813 | 8/1996 |
| WO | WO 97/08193 | 3/1997 |
| WO | 98/50421 * | 11/1998 |
| WO | WO 99/11606 A3 | 3/1999 |
| WO | WO 00/73326 | 12/2000 |

OTHER PUBLICATIONS

Kemeny (Seminars in Oncology 21 (4 Suppl 7) 67-75, 1994).*
Newton (Expert Opinion on Investigational Drugs 9 (12) 2815-29, 2000).*
Giese (Journal of Cancer Research and Clinical Oncology 127 (4) 217-25, 2001).*
Ragnhammar (Acta Oncologica 40 (2□3) 282-308, 2001).*
Garattini (European Journal of Cancer 37 Suppl 8 S128-47, 2001).*
Bardelli (Oncogene 18, 1139-1146, 1999).*
Ye et al., "L-O-(2-Malonyl)tyrosine" A New Phosphotyrosyl Mimetic for the Preparation of Src Homology 2 Domain Inhibitory Peptides, J. Med. Chem. vol. 38, pp. 4270-4275, 1995.
Burke, Jr., et al., "4'-O-[2-(2-Fluoromalonyl)]-L-tyrosine: A Phosphotyrosyl Mimic for the Preparation of Signal Transduction Inhibitory Peptides", J. Med. Chem., vol. 39, pp. 1021-1027, Mar. 1, 1996.
Schoepfer et al., "Structure-based Design of Peptidomimetic Ligands of Grb2-SH2 Domain", Bioorganic & Medicinal Chemistry Letters 8, pp. 2865-2870, 1998.
Yao et al., "Potent Inhibition of Grb2 SH2 Domain Binding by Non-Phosphate-Containing Ligands", J. Med. Chem., vol. 42, pp. 25-35, 1999.
Gay et al., "Effect of Potent and Selective Inhibitors of the Grb2 SH2 Domain on Cell Motility", The Journal of Biological Chemistry, vol. 274, pp. 23311-23315, Aug. 13, 1999.
Schoepfer et al., "Highly Potent Inhibitors of the Grb2-SH2 Domain", Bioorganic & Medicinal Chemistry Letters 9, pp. 221-226, 1999.
Burke, Jr., et al., Monocarboxylic-Based Phosphotyrosyl Mimetics in the Design of Grb2 SH2 Domain Inhibitors, Bioorganic & Medicinal Chemistry Letters 9, pp. 347-352, 1999.
Gilmer et al., "Peptide Inhibitors of src SH3-SH2-Phosphorprotein Interactions", The Journal of Biological Chemistry, vol. 269, pp. 31711-31719, Dec. 16, 1994.
Charifson et al., "Peptide Ligands of pp60$^{c-src}$ SH2 Domains: A Thermodynamic and Structural Study", Biochemistry, vol. 36, pp. 6283-6293, 1997.
Liu et al., "Synthesis of L-2,3,5,6-Tetrafluoro-4-(Phosphonomethyl) Phenylalanine, a Novel Non-Hydrolyzable Phosphotyrosine Mimetic and L-4-(Phosphonodifluoromethyl)Phenylalanine", Tetrahedron Letters, vol. 38, pp. 1389-1392, 1997.
Cleland, "The Meerwein Reaction in Amino Acid Synthesis. II. An Investigation of Twenty-one Substituted Anilines", The Journal of Organic Chemistry, Vo., 34, pp. 744-747, Mar. 1969.
Gao et al., Inhibition of Grb2 SH2 Domain Binding by Non-Phosphate-Containing Ligands. 2. 4-(2-Malonyl)phenylalanine as a Potent Phosphotyrosyl Mimetic, J. Med. Chem., vol. 43, pp. 911-920, 2000.
Furet et al., Stucture-Based Desing and Synthesis of High Affinity Tripeptide Ligands of the Grb2-SH2 Domain, J. Med. Chem., vol. 41, pp. 3442-3449, 1998.

Tong et al., "Carboxymethyl-phenylalanine as a Replacement for Phosphotyrosine in SH2 Domain Binding", The Journal of Biological Chemistry, vol. 273, pp. 20238-20242 Aug. 7, 1998.
Tulasne et al., "The Multisubstrate Docketing Site of the MET Receptor is Dispensable for MET-mediated RAS Signaling and Cell Scattering", Molecular Biology of the Cell, vol. 10, pp. 551-565, Mar. 1999.
Kim et al., "Dual Signaling Role of the Protein Tyrosine Phosphotase SHP-2 in Regulating Expression of Acute-Phase Plasma Proteins by Interleukin-6 Cytokine Receptors in Hepatic Cells", Molecular and Cellular Biology, vol. 19, pp. 5326-5338, Aug. 1999.
Nguyen et al., "Association of the Multisubstrate Docking Protein Gab1 with the Hepatocyte Growth Factor Receptor Requires a Functional Grb2 Binding Site Involving Tyrosine 1356", The Journal of Biological Chemistry, vol. 272, pp. 20811-20819, Aug. 15, 1997.
Maina et al., "Uncoupling of Grb2 from the Met Receptor in Vivo Reveals Complex roles in Muscle Development", Cell, vol. 87, pp. 531-542, Nov. 1, 1996.
Ponzetto et al., "Specific Uncoupling of GRB2 from the Met Receptor", The Journal of Biological Chemistry, vol. 271, pp. 14119-14123, Jun. 14, 1996.
Ettmayer et al., "Structural and Conformational Requirements for High-Affinity Binding to the SH2 Domain of Grb2", J. Med. Chem., vol. 42, pp. 971-980, 1999.
Royal et al., "Differential Requirement of Grb2 and P13-Kinase in HGF/SF-Induced Cell Motility and Tubulogenesis", Journal of Cellular Physiology, vol. 173, pp. 196-201, 1997.
Gao et al., Biorg and Med Chem Lett. 10, 923-927 (2000).
Burke, Jr., et al., "Preparation of . . . Peptide Synthesis", J. of Synthetic Organic Chem., No. 11, p. 1019, Nov. 11,1991.
Burke, Jr., et al., "Potent Inhibition of Grb2 SH2 domain Binding by Non-Phosphate containing Ligands", First Annual Meeting on the Experimental Therapeutics of Human Cancer, Jun. 11-13, 1998, Hood College, Frederick Maryland (Summary).
Katunuma et al., "Use of new synthetic substrates for assays of cathepsin L and cathepsin B", J. Biochem. (Tokyo), vol. 93, pp. 1129-1135, 1983 (Abstract only).
Burke, Jr., et al., "Enantioselective Synthesis . . . Inhibitory Peptides", Tetrahedron, vol. 54, pp. 9981-9994, 1998.
Burke, Jr., et al., "Phosphotyrosyl-Based Motifs in the Stucture-Based Design of Protein-Tyrosine Kinase-Dependent Signal Transduction Inhibitors", Current Pharmaceutical Design, vol. 3, pp. 291-304, 1997.
Burke, Jr., et al., "Nonhydrolyzable Phosphotyrosly Mimetics for the Preparation of Phosphatase-Resistant SH2 Domain Inhibitors", Biochemistry, vol. 33, pp. 6490-6494, 1994.
Ye et al., "L-O-(2-Malonyl)tyrosine (L-OMT) a New Phosphotyrosyl Mimic Suitably Protected for Solid-Phase Synthesis of Signal Transduction Inhibitory Peptides", Tetrahedron Letters, vol. 36, pp. 4733-4736, 1995.
Kuriyan, "Modular Peptide recognition Domains in Eukaryotic Signaling", Annu. Rev. Biophys. Biomol. Struct., vol. 26, pp. 259-288, 1997.
Mayer et al., "Functions of SH2 and SH3 Domains", Protein modules in signal transduction, edited by A. J. Pawson, Berlin, New York, Springer, c1998, pp. 1-22.
Fry et al., "New insights into protein-tyrosine kinase receptor signaling complexes", Protein Science, vol. 2, pp. 1785-1797, 1993.
Levitzki, "Targeting signal transduction for disease therapy", Current Opinion in Cell Biology, vol. 8, pp. 239-244, 1996.
Boutin, "Tyrosine Protein Kinase Inhibition and Cancer", Int. J. Biochem., vol. 26, pp. 1203-1226, 1994.
Levizski et al., "Tyrosine Kinase Inhibition: An Approach to Drug Development", Science, vol. 267, pp. 1782-1788, Mar. 24, 1995.
Lawrence et al., "Protein Kinase Inhibitors: The Tyrosine-specific Protein Kinases", Pharmacol. Ther., vol. 77, pp. 81-114, 1998.
Burke, Jr., et al., "Protein-Tyrosine Phosphatases: Structure, Mechanism, and Inhibitor Discovery", Biopolymers (Peptide Science), vol., 47, pp. 225-241 (1998).

Schoelson, "SH2 and PTB domain interactions in tyrosine kinase signal transduction", Current Opinion in Chemical Biology, vol. 1, pp. 227-234, 1997.

Waksman et al., "Crystal structure of the phosphotyrosine recognition domain Sh2 of v-src complexed with tyrosine-phosphorylated peptides", Nature, vol. 358, pp. 646-653, Aug. 20, 1992.

Waksman et al., "Binding of High Affinity Phosphotyrosyl Peptide to the Src SH2 Domain: Crystal Structues of the Complexed and Peptide-free Forms", Cell, vol. 72, pp. 779-790, Mar. 12, 1993.

Mikol et al., "The Crystal Structure of the SH2 Domain of p56[ick] Complexed with Two Phosphonopeptides Suggest a Gated Peptide Binding Site", J. Mol. Biol. vol. 246, pp. 344-355, 1995.

Hatada et al., "Molecular basis for interaction of the protein tyrosine kinase ZAP-70 with the T-cell receptor", Nature, vol. 377, pp. 32-38, Sep. 7, 1995.

Zhou et al., "Solution structure of the Shc SH2 domain complexed with a tyrosine-phosphorylated peptide from the T-cell receptor", Proc. Natl. Acad. Sci., vol. 92, pp. 7784-7788, Aug. 1995.

Narula et al., "Solution structure of the C-terminal SH2 domain of the human tyrosine kinase Syk complexed with a phosphotyrosine pentapeptide", Structure, vol. 3, 1061-1073, Oct. 15, 1995.

Xu et al., "Solution Structure of the Human pp60[c-src] SH2 Domain Complexed with a Phosphorylated Tyrosine Pentapeptide", Biochemistry, vol. 34, pp. 2107-2121, 1995.

Tong et al., "Cyrstal Structures of the Human p56[lck] SH2 Domain in Complex with Two Short Phosphotyrosyl Peptides at 1.0 Å and 1.8 Å Resolution", Academic Press Limited, 10 pages, 1996.

Sicheri et al., "Crystal structure of the Src family tyrosine kinase Hck", Nature, vol. 385, pp. 602-609, Feb. 13, 1997.

Chen et al., "Crystal Structure of a Tyrosine Phosphorylated STAT-1 Dimer Bound to DNA", Cell, vol. 93, pp. 827-839, May 29, 1998.

Songyang et al., "Recognition and specificity in protein tyrosine kinase-mediated signalling", Elsevier Science Ltd., pp. 470-475, 1995.

Lunney et al., "Structure-Based Design of a Novel Series of Nonpeptide Ligands That Bind to the pp60[src] SH2 Domain", J. Am. Chem. Soc., vol. 119, pp. 12471-12476, 1997.

Pacofsky et al., "Potent Dipeptide Inhbitors of the pp60[c-src] SH2. Domain", J. Med. Chem., vol. 41, pp. 1894-1908, 1998.

Marseigne et al., "Synthesis of New Amino Acids Mimicking Sulfated and Phosphorylated Tyrosine Residues", J. Org. Chem., vol. 53, pp. 3621-3624, 1988.

Domchek et al., "Inhibition of SH2 Domain/Phosphoprotein Association by a Nonhydrolyzable Phosphonopeptide", Biochemistry, vol. 31, pp. 9865-9870, 1992.

Xiao et al., "Syp (SH-PTP2) Is a Positive Mediator of Growth Factor-stimulated Mitogenic Signal Transduction", The Journal of Biological Chemistry, vol. 269, pp. 21244-21248, Aug. 19, 1994.

Wange et al., "$F_2(Pmp)_2$-$TAMs_3$, a Novel Competitive Inhibitor of the binding of ZAP-70 to the T Cell Antigen Receptor, Blocks Early T Cell Signaling", JBC Online, vol. 270, pp. 944-948, Jan. 13, 1995.

Rojas et al., Controlling Epidermal Growth Factor (EGF)-stimulated Ras Activation in Intact Cells by a Cell-permeable Peptide Mimicking Phosphorylated EGF Receptor The Journal of Biological Chemistry, vol. 271, pp. 27456-27461, Nov. 1, 1996.

Williams et al., "Selective Inhibition of Growth Faxtor-stimulated Mitogenesis by a Cell-permeable Grb2-binding Peptide", The Journal of Biological Chemistry, vol. 272, pp. 22349-22354, Aug. 29, 1997.

Stankovic, "The Role of 4-Phosphonodifluoromethyl- and 4-Phosphono-Phenylalanine in the Selectivity and Cellular Uptake of SH2 domain Ligands", Bioorganic & Medicinal Chemistry Letters, vol. 7, pp. 1909-1914, 1997.

Mehrotra et al., "α-Dicarbonyls as "Non-Charged" Arginine-Directed Affinity Labels", Bioorganic & Medicinal Chemistry Letters, vol. 6, pp. 1941-1946, 1996.

Margolis, "The GRB Family of SH2 domain Proteins", Prog. Biophys. Molec. Biol., vol. 62, pp. 223-244, 1994.

Burke, Jr., et al., "Preparation of Fluoro- and Hyrdoxy-4-(phosphonomethyl)-D,L-phenylalanine Suitable Protected for Solid-Phase Synthesis of Peptides Containing Hydrolytically Stable Analogues of O-Phosphotyrosine", Jour. Of Organic Chemistry, pp. 1336-1340, Mar. 12, 1993.

Burke, Jr., et al., "Synthesis of 4-Phosphono(difluoromethyl)-D,L-phenyllanine and N-Boc and N-Fmoc Derivatives Suitably Protected for solid-Phase Synthesis of Nonhydorlyzable Phosphotyrosyl Peptide Analogues", Tetrahedron Letters, vol. 34, pp. 4125-4128, 1993.

Smyth et al., "Enanthioselective Synthesis of N-Boc and N-Fmoc Protected Diethyl 4-Phosphono(difluoromethyl)-L-Phenylalanine; Agents Suitable for the Solid-Phase Synthesis of Peptides Containing Nonhydrolyzable Analogues of O-Phosphotyrosine", Tetrahedron letters, vol. 35, pp. 551-554, 1994.

Miller et al., "EPSP Synthase . . . 3-Phosphate Mimics", J. Organic & Medicinal Chem. Letters, vol. 3, No. 7, pp. 1435-1440, 1993.

"Synthesis and . . . containing peptides", Chem. Abs., vol. 123, No. 257331h, p. 1220, 1995.

Furet et al., "Discovery of 3-Aminobenzyloxycarbonyl as an N-Terminal Group conferring High Affinity to the Minimal Phosphopeptide Sequence Recognized by the Grb2-SH2 Domain", J. Med. Chem., vol. 40, pp. 3551-3556, 1997.

Rahuel et al., "Structural Basis for the High Affinity of Amino-Aromatic SH2 Phosphopeptide Ligands", J. Mol. Biol., 279, pp. 1013-1022, 1998.

Garcia-Echeverria et al., "Potent Antagonists of the SH2 Domain of Grb2: Optimization of the $X_{+1}$-Position of 3-Amino-Z-Tyr($PO_3H_2$)-$X_{=1}$-Asn-$NH_2$", Journal of Medicinal Chemistry, vol. 41, pp. 1741-1744, May 21, 1998.

Rahuel et al., "Structural basis for specificity of GRB2-SH2 revealed by a novel ligand binding mode", nature Structural Biology, vol. 3, No. 7, pp. 586-589, Jul. 7, 1996.

Oligino et al., "Nonphosphorylated . . . 2 Domain", The J. of Biological Chem., vol. 272, No. 46, pp. 29046-29052, Nov. 14, 1997.

Allen et al., "Tritiated Peptides. Part 15. Synthesis of Tritium Labelled Biologically Active Analogues of Somatostatin", J. Chem. Soc., Perkin Trans. 1, pp. 989-1003, 1986.

Ben-Levy et al., "A single autophosphorylation site confers oncogenicity to the Neu/ErbB-2 receptor and enables coupling to the MAP Kinase pathway", The EMBO Journal, vol. 13, pp. 3302-3311, 1994.

Dankort et al., Distinct Tyrosine Autophosphorylation Sites Negatively and Positively Modulate New-Mediated Transformation, Molecular and Cellular Biology, vol. 17, pp. 5410-5425, Sep. 1997.

Ma et al., "Bcr phosphorylated on tyrosine 177 binds Grb2", Oncogene, vol. 14, pp. 2367-2372, 1997.

DiFiore et al., "Overexpression of the Human EGF Receptor confers an EGF-Dependent Transformed Phenotype to N1H 3T3 Cells", Cell, vol. 51, pp. 1063-1070, Dec. 24, 1987.

Hudziak et al, "Increased expression of the putative growth factor receptor p185[HER2] causes tranformation and tumorigenesis of NIH 3T3 cells", Proc. Natl. Acad. Sci., vol. 84, pp. 7159-7163, Oct. 1987.

Kraus et al., "Overexpression of the EGF receptor-related proto-oncogene erbB-2 in human mammary tumor cells lines by different molecular mechanisms", The EMBO Journal, vol. 6, pp. 605-610, 1987.

Sastry et al., "Quantitative analysis of Grb2-Sos1 interaction: the N-terminal SH3 domain of Grb2 mediates affinity", Oncogene, 11, pp. 1107-1112, 1995.

Searles, The Reaction of Trimethylene Oxide with Grignard Reagents and Organolithim Compounds, J. Amer. Chem. Soc., vol. 73, pp. 124-125, 1951.

Fretz et al., "Targeting a Hydrophobic Patch on the Surface of the Grb2-SH2 Domain", 15th Amer. Peptide Symposium, Nashville, TN, Jun. 1997, Abstract No. P422.

Fixman et al., "Efficient Cellular . . . Proteins, Cb1 and Gab1", The J. of Biological Chem., vol. 272, No. 32, pp. 20167-20172, Aug. 8, 1997.

Tari et al., "Inhibition of Grb2 . . . Leukemic Cells", Biochemical and Biophysical Research Communications, vol. 235, pp. 383-388, Article No. RC976791, 1997.

Xie et al., "Dominant-negative Mutants . . . Rat HER-2/Neu", The J. of Biological Chem., vol. 270, No. 51, pp. 30717-30724, Dec. 22, 1995.

Maignan et al., "Crystal Structure of the Mammalian Grb2 Adaptor", Science, vol. 268, pp. 291-293, Apr. 14, 1995.

Saltiel et al., "Targeting signal transduction in the discovery of antiproliferative drugs", Chemistry & Biology, vol. 3, No. 11, pp. 887-893, Nov. 1996.

McNemar et al., Thermodynamic and . . . Binding to Grb2-SH2:, Biochemistry, vol. 36, pp. 10006-10014, 1997.

Ogura et al., "Conformation of an . . . Grb2 SH2 domain", J. of Biomolecular NMR, vol. 10, pp. 273-278, 1997.

Gay et al., "Dual Specificity of . . . Peptide Ligands", Biochemistry, vol. 36, pp. 5712-5718, 1997.

Bobko et al., "CD45 Protein . . . Irreversible Inhibitors", Bioorganic & Medicinal Chem. Letters, vol. 5, No. 4, pp. 353-356, 1995.

Burke et al., "Conformationally Constrained . . . 2 Domain Inhibitors", J. Med. Chem., vol. 38, pp. 1386-1396, 1995.

Chemical Abstracts, vol. 122, p. 424, 1995 (Abs. No. 258899).

Gordeev et al., "N-α-Fmoc-4-Phosphono(difluoromethyl)-L-phenylalanine: . . . into Peptides", Tetrahedron Letters, vol. 35, pp. 7585-7588, 1994.

Kitas et al., "Synthesis of O-Phosphotyrosine . . . Deportection Procedures", J. Org. Chem., vol. 55, pp. 4181-4187, 1990.

Chemical Abstracts, vol. 124, No. 1, p. 1004, 1996 (Abs. No. 9413).

Morelock et al., "Determination of Receptor . . . Phosphotyrosyl Peptides", J. of Med. Chem., vol. 38, pp. 1309-1318.

Shahripour et al., "Novel Phosphotyrosine . . . Domain", Bioorganic & Medicinal Chem. Letters, vol. 6, No. 11, pp. 1209-1214, 1996.

Rojas et al., "An Alternative . . . SH2 Domain", Biochemical and Biophysical Research Communications, vol. 234, pp. 675-680, 1997.

Jiang et al. "Hepatocyte growth factor/scatter factor, its molecular, cellular and clinical implications in cancer", Critical Reviews in Oncology/Hematology, 29:209-248 (1999).

Kim et al., *FEBS Lett., 453*, 174-178, 1999.

Yao et al., *Tetrahedron*, 55, 2865-2874 (1999).

* cited by examiner i). 1. (COCl)$_2$, 2. t-Butanol, 92.8%; ii). H$_2$, Pd black, EtOH, 100%; iii). Ac$_2$O, Pyr., 94%; iv). NBS (BzO)$_2$, 38.8%; v). William's reagent. LiHMDS, THF, -78°C-R.T., 50.5%; vi) H$_2$, Pd Black, EtOH-THF, 100%; vii). Fmoc-Osu, NaHCO$_3$, Dioxane-H$_2$O, 39.5%

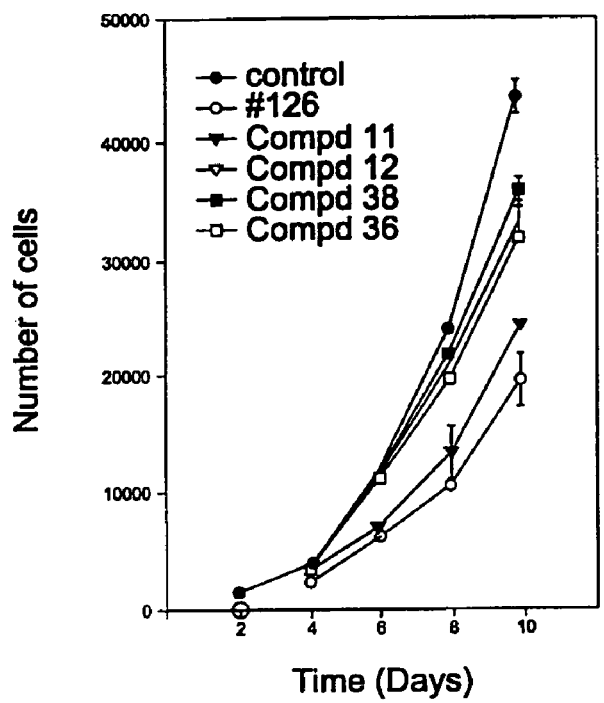
FIG. 17a
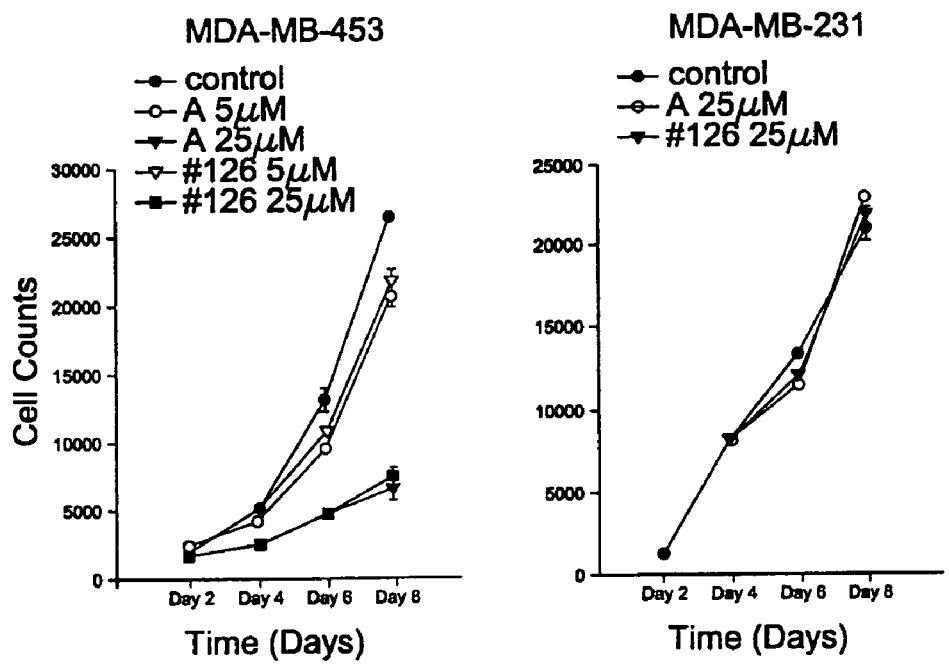
FIG. 17b
FIG. 17c

Compd 126

Compd A

PHENYLALANINE DERIVATIVES

This is the national stage of PCT/US00/08231, filed Mar. 23, 2000, which claims the benefit of U.S. Provisional Patent Application No. 60/126,047, filed Mar. 23, 1999, the disclosure of which is incorporated by reference.

TECHNICAL FIELD OF THE INVENTION

The present invention relates to novel phenylalanine derivatives, compositions, and a method of using these derivatives in inhibiting SH2 domain binding with a phosphoprotein. The present invention further provides precursors suitable for preparing the phenylalanine derivatives.

BACKGROUND OF THE INVENTION

The pharmaceutical industry is in search for new classes of compounds for the therapy and prophylaxis of proliferative diseases such as cancer, autoimmune diseases, and hyperproliferative skin disorders such as psoriasis. These diseases or disorders affect a large portion of the population, leading to suffering and possibly death.

Some of these diseases or disorders may involve signal transduction. Signal transduction is critical to normal cellular homeostasis and is the process of relaying extracellular messages, e.g., chemical messages in the form of growth factors, hormones and neurotransmitters, via receptors, e.g., cell-surface receptors, to the interior of the cell. Protein-tyrosine kinases play a central role in this biological function. Among others, these enzymes catalyze the phosphorylation of specific tyrosine residues to form tyrosine phosphorylated residues. Examples of this class of enzymes include the PDGF receptor, the FGF receptor, the HGF receptor, members of the EGF receptor family such as the EGF receptor, erb-B2, erb-B3 and erb-B4, the src kinase family, Fak•kinase and the Jak kinase family. The tyrosine-phosphorylated proteins are involved in a range of metabolic processes, from proliferation and growth to differentiation.

Protein-tyrosine phosphorylation is known to be involved in modulating the activity of some target enzymes as well as in generating specific complex networks involved in signal transduction via various proteins containing a specific amino acid sequence called a Src homology region or SH2 domain (see *Proc. Natl. Acad. Sci. USA*, 90, 5891 (1990)). A malfunction in this protein-tyrosine phosphorylation through tyrosine kinase overexpression or deregulation is manifested by various oncogenic and (hyper-)proliferative disorders such as cancer, inflammation, autoimmune disease, hyperroliferative skin disorders, such as psoriasis, and allergy/asthma.

SH2- and/or SH3- comprising proteins that play a role in cellular signaling and transformation include, but are not limited to, the following: Src, Lck, Eps, ras GTPase-activating protein (GAP), phospholipase C, phosphoinositol-3 (Pl-3)kinase, Fyn, Lyk, Fgr, Fes, ZAP-70, Sem-5, p85, SHPTP1, SHPTP2, corkscrew, Syk, Lyn, Yes, Hck, Dsrc, Tec, Atk/Bpk, Itk/Tsk, Arg, Csk, tensin, Vav, Emt, Grb2, BCR-Abl, Shc, Nck, Crk, CrkL, Syp, Blk, 113TF, 91TF, Tyk2, especially Src, phospholipase c, phosphoinositol-3 (pl-3) kinase, Grb2, BCR-Abl, Shc, Nck, Crk, CrkL, Syp, Blk, 113TF, 91TF, and Tyk2. A direct link has been established between activated receptor kinases and Ras with the finding that the mammalian Grb2 protein, a 26 kilodalton (kD) protein comprising a single SH2 and two SH3 domains bind to proline-rich sequences present in the Sos exchange factor.

The significance of ras-regulatory proteins in human tumors is also highlighted by the critical role of Grb2 in BCR-Abl mediated oncogenesis (*J. Exp. Med.*, 179, 167–175 (1994)).

Central to the binding of SH2 domains with phosphotyrosine ("ptyr") containing ligands is the interaction of the doubly ionized ptyr phosphate with two invariant arginine residues in a well formed pocket. These arginine-phosphate interactions are particularly critical to the overall binding, such that high affinity binding is usually lost by removal of the phosphate group.

Although the ptyr pharmacophore plays a dominant role in SH2 domain-ligand interactions, ptyr residues are not suitable components of inhibitors intended for in vivo application, due to the enzymatic lability of the phosphate ester bond and the poor cellular penetration of doubly ionized phosphate species.

In view of the foregoing, there exists a need for molecules that have an ability to mimic the structure of the phosphotyrosine peptide binding site, as well as a need for compounds that have the ability to disrupt the interaction between SH2 domains of proteins (e.g., regulatory proteins) for example that of Grb2, and proteins with phosphorylated moieties. There also exists a need for suitable starting materials or precursors in the synthesis of the molecules that inhibit binding of SH2 domains. There further exists a need for compounds suitable for use in the therapy or prophylaxis of proliferative diseases or conditions, as well as in diagnosis, assays, and testing.

These advantages of the present invention will be apparent from the detailed description of the embodiments of the invention set forth below.

BRIEF DESCRIPTION OF THE DRAWINGS

FIGS. 17a–c depict the human breast cancer cell growth and proliferation inhibition by compounds 11, 12, 36, and 38. FIG. 17a depicts the proliferation inhibition of human breast cancer cells MDA-MB-453; FIG. 17b depicts growth inhibition of MDA-MB-453; and FIG. 17c depicts lack of growth inhibition of MDA-MB-253 breast cancer cells.

BRIEF SUMMARY OF THE INVENTION

Figure 1:
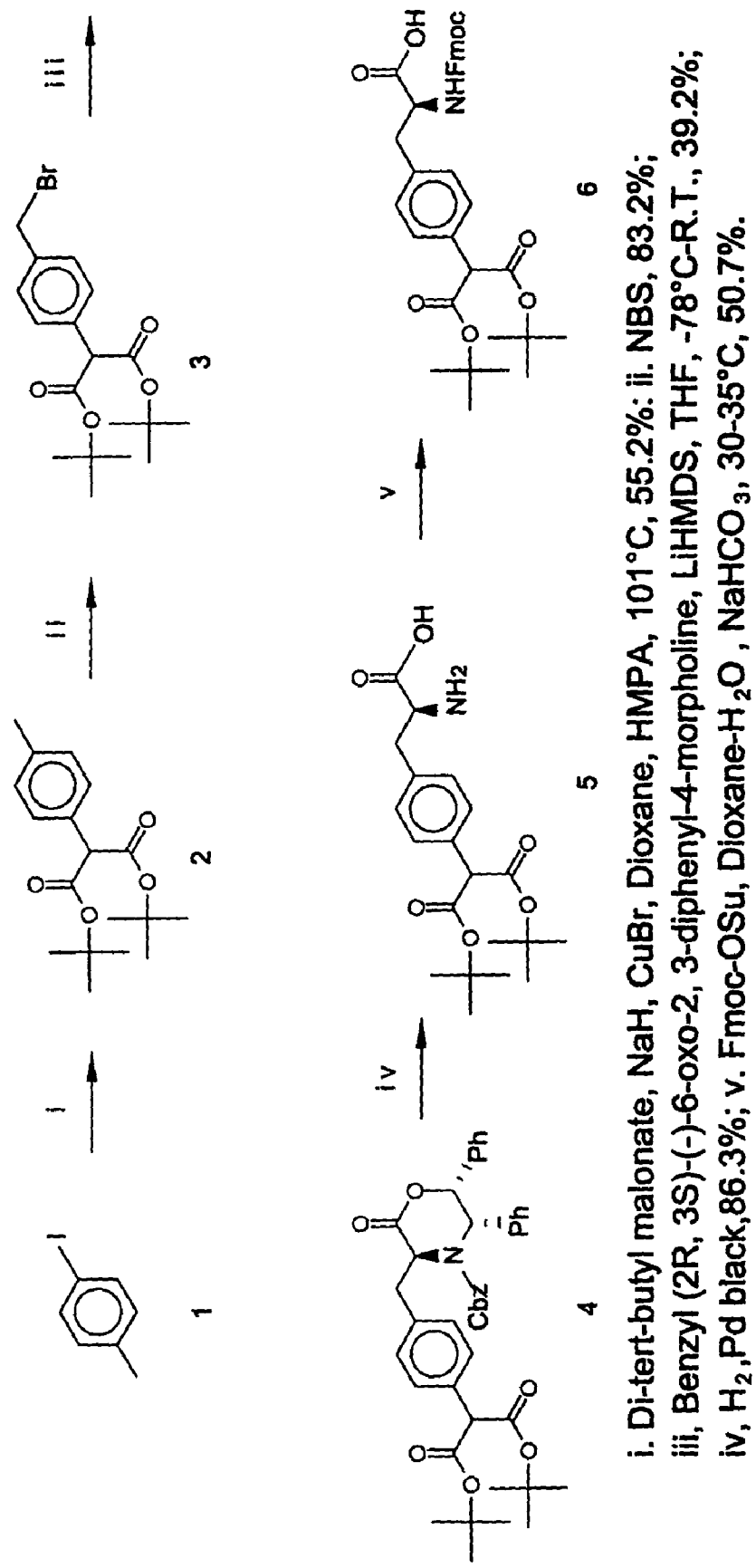
FIG. 1 schematically depicts a route for preparing compounds 1–5.

The prevent invention provides a compound of formula I:

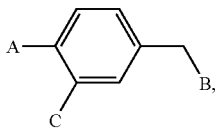

(I)

wherein:

A is carboxyl, carboxylalkyl, dicarboxylalkyl, alkoxycarbonyl, alkoxycarbonylalkyl, dialkoxycarbonylalkyl, or a malonyl group of formula II:

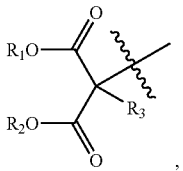

(II)

wherein $R_1$ and $R_2$ may be the same or different and are selected from the group consisting of hydrogen, alkyl, aryl, arylalkyl, alkylaryl, and heteroaryl; and $R_3$ is selected from the group consisting of hydrogen, halo, hydroxy, amino, alkyl, aryl, and alkoxy;

B has the formula III: B has the formula III:

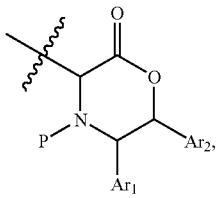

(III)

wherein P is an amine protecting group; and $Ar_1$ and $Ar_2$ are aryl groups; or the formula IV:

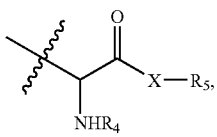

(IV)

wherein X is NH or O; $R_4$ is hydrogen, alkyl, aryl, alkylaryl, arylalkyl, or an amine protective group; and $R_5$ is selected from the group consisting of hydrogen, alkyl, aryl, arylalkyl, alkylaryl, and heteroaryl; and C is selected from the group consisting of hydrogen, hydroxyl, alkyl, alkylcarbonyl, alkylcarbonyloxy, alkoxycarbonyl, and alkoxycarbonyl alkyl;

wherein said aryl, heteroaryl, and the aryl portion of said arylalkyl and alkylaryl may be unsubstituted or substituted with a substituent selected from the group consisting of alkyl, hydroxy, halo, keto, amino, and alkoxy; with the provisos that (i) $R_5$ is not hydrogen when A is carboxyl or carboxylalkyl, C is hydrogen, B has the formula IV wherein $R_4$ is hydrogen or alkylcarbonyl, and X is NH; and (ii) $R_5$ is not hydrogen or alkyl when A is carboxyl or carboxyalkyl, C is hydrogen or hydroxy, B has the formula IV wherein $R_4$ is hydrogen or alkylcarbonyl, and X is O.

The present invention further provides a process for the preparation of a compound of formula VII:

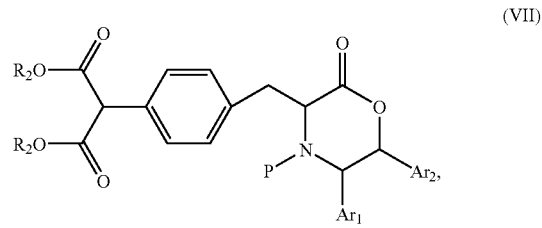

(VII)

wherein $R_2$ is alkyl, P is an amine protecting group, $Ar_1$ and $Ar_2$ are aryl; the process comprising:

(a) converting a p-halotoluene to a p-tolyl-malonic acid dialkyl ester by contacting the p-halotoluene with a dialkylmalonate and a cuprous halide;

(b) halogenating the p-tolyl-malonic acid dialkyl ester to obtain a (4-halomethylphenyl)-malonic acid dialkyl ester; and (c) contacting the (4-halomethylphenyl)-malonic acid dialkyl ester with a benzyl-6-oxo-2,3-diaryl-4-morpholine to obtain the compound of formula VII.

The present invention further provides a process for preparing a compound of formula VIII:

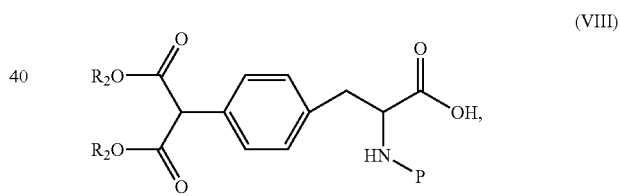

(VIII)

wherein $R_2$ is alkyl and P is an amine protecting group; the process comprising:

(a) reducing the compound of formula VII to obtain a compound of formula IX

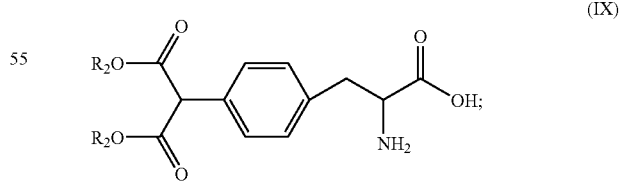

(IX)

and (b) reacting the compound of formula IX with an amine protecting agent to obtain the compound of formula VIII.

The present invention further provides a conjugate comprising a conjugant covalently linked to the compounds of formula I.

The present invention further provides a compound of formula X:

$$W—Y—(AA)_n—Z \quad (X)$$

wherein n is 0 to 15, Y is a phenylalanyl radical having a phenyl ring, an amine end, and a carboxyl end, and the phenyl ring having one or more substituents selected from the group consisting of hydroxyl, carboxyl, formyl, carboxylalkyl, carboxylalkyloxy, dicarboxyalkyl, dicarboxyalkyloxy, dicarboxyhaloalkyl, dicarboxyhaloalkyloxy, and phosphonoalkyl, phosphonohaloalkyl, wherein the alkyl portion of the substituents may be unsubstituted or substituted with a substituent selected from the group consisting of halo, hydroxy, carboxyl, amino, aminoalkyl, alkyl, alkyloxy, and keto;

W is a moiety attached to the nitrogen of Y and is selected from the group consisting of alkylcarbonyl, oxalyl, carboxyalkyl carbonyl, heterocyclyl carbonyl, heterocyclylalkyl carbonyl, arylalkyl heterocyclylalkyl carbonyl, aryloxycarbonyl, and arylalkoxycarbonyl, wherein the aryl and alkyl portions of the substituents may be unsubstituted or substituted with a substituent selected from the group consisting of halo, hydroxy, carboxyl, amino, aminoalkyl, alkyl, alkoxy, and keto; and the heterocyclyl portion of W contains at least 4 hetero atoms selected from the group consisting of O, N and S;

AA is an amino acid, the amine end of which is attached to the carboxyl end of Y; and Z is an arylalkylamino or arylheterocyclyl alkylamino; or a salt thereof;

with the proviso that W is not arylalkylamino when the phenyl ring of phenylalanyl contains a phosphonoalkyl or phosphonohaloalkyl substituent at a position para to the alkylamido group and the ortho and meta positions are unsubstituted.

The present invention further provides (a) a composition comprising a pharmacologically acceptable carrier and a compound of formula X, (b) a method of inhibiting an SH2 domain from binding with a protein such as a phosphoprotein comprising contacting an SH2 domain or a sample or substance containing an SH2 domain with a compound of formula X, and (c) compound of formula X for use in medicine. Compounds of formula X find use in the manufacture of a medicament for the treatment of a condition that responds to the inhibition of phosphoprotein binding to an SH2 domain of a mammal. The present invention further provides a method for determining the presence of an SH2 domain in a material comprising:

(a) exposing a sample of the material to a SH2 binding compound and obtaining a first binding result;

(b) exposing another sample of the material to a conjugate or compound of formula X and obtaining a second binding result; and (c) comparing the first and second binding results to determine whether an SH2 domain is present in the material.

The present invention further provides a method of preventing or treating a disease, state, or condition in a mammal that involves an SH2 domain binding comprising administering to the mammal a compound of the present invention. The present invention further provides a method of enhancing the therapeutic effect of a treatment rendered to a mammal that has been afflicted with a disease, state, or condition, comprising administering to the mammal a compound of the present invention in conjunction with the treatment.

While the invention has been described and disclosed below in connection with certain embodiments and procedures, it is not intended to limit the invention to those specific embodiments. Rather it is intended to cover all such alternative embodiments and modification as fall within the spirit and scope of the invention.

DETAILED DESCRIPTION OF THE EMBODIMENTS

The present invention provides certain novel phenylalanine conjugates useful in a variety of applications, especially in the treatment or prophylaxis of various diseases or conditions in a mammalian body. Particular examples of such conjugates are phenylalanine peptide conjugates. The present invention further provides phenyl alanine precursors that can be conveniently used in the synthesis of phenylalanine peptide conjugates. Thus, the present invention provides a precursor compound of formula I:

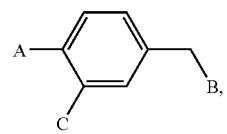

C is selected from the group consisting of hydrogen, hydroxyl, alkyl, alkylcarbonyl, alkylcarbonyloxy, alkoxycarbonyl, and alkoxycarbonyl alkyl;

wherein said aryl, heteroaryl, and the aryl portion of said arylalkyl and alkylaryl may be unsubstituted or substituted with a substituent selected from the group consisting of alkyl, hydroxy, halo, keto, amino, and alkoxy; with the provisos that (i) $R_5$ is not hydrogen when A is carboxyl or carboxyalkyl, C is hydrogen, B has the formula IV wherein $R_4$ is hydrogen or alkylcarbonyl, and X is NH; and (ii) $R_5$ is not hydrogen or alkyl when A is carboxyl or carboxyalkyl, C is hydrogen or hydroxy, B has the formula IV wherein $R_4$ is hydrogen or alkylcarbonyl, and X is O.

The alkyl portion of the various groups described above can have any suitable number of carbon atoms, e.g., from 1 to about 12 carbon atoms, preferably from 1 to 6 carbon atoms, and more preferably from 1 to 4 carbon atoms. The aryl portion of the various groups described can have any number of aromatic rings, e.g., from 1 to 3 rings, preferably 1 or 2 rings, and more preferably 1 ring. Thus, for example, the present invention provides a compound of formula I wherein:

A is carboxyl, carboxyl $C_1$–$C_6$ alkyl, dicarboxy $C_1$–$C_6$ alkyl, $C_1$–$C_6$ alkoxycarbonyl, $C_1$–$C_6$ alkoxycarbonyl $C_1$–$C_6$ alkyl, $C_1$–$C_6$ dialkoxycarbonyl $C_1$–$C_6$ alkyl, or a malonyl group of formula II wherein $R_1$ and $R_2$ may be the same or different and are selected from the group consisting of hydrogen, $C_1$–$C_6$ alkyl, aryl, aryl $C_1$–$C_6$ alkyl, $C_1$–$C_6$ alkylaryl, and heteroaryl; and $R_3$ is selected from the group consisting of hydrogen, halo, hydroxy, amino, $C_1$–$C_6$ alkyl, aryl, and $C_1$–$C_6$ alkoxy;

B has the formula III wherein P is an amine protecting group; and $Ar_1$ and $Ar_2$ are aryl groups; or the formula IV, wherein X is NH or O; $R_4$ is hydrogen, $C_1$–$C_6$ alkyl, aryl, $C_1$–$C_6$ alkylaryl, aryl $C_1$–$C_6$ alkyl, or an amine protective group; and $R_5$ is selected from the group consisting of hydrogen, $C_1$–$C_6$ alkyl, aryl, aryl $C_1$–$C_6$ alkyl, $C_1$–$C_6$ alkylaryl, and heteroaryl; and C is selected from the group consisting of hydrogen, hydroxyl, $C_1$–$C_6$ alkyl, $C_1$–$C_6$ alkylcarbonyl, $C_1$–$C_6$ alkylcarbonyloxy, $C_1$–$C_6$ alkoxycarbonyl, and $C_1$–$C_6$ alkoxycarbonyl $C_1$–$C_6$ alkyl; wherein the aryl, heteroaryl, and the aryl portion of the arylalkyl and alkylaryl may be unsubstituted or substituted with a substituent selected from the group consisting of $C_1$–$C_6$ alkyl, hydroxy, halo, keto, amino, and $C_1$–$C_6$ alkoxy.

The asymmetric carbons in B can have any suitable configuration. Specifically, B can have the R, S, or R and S configurations. Thus, B in formula III can have the following structures:

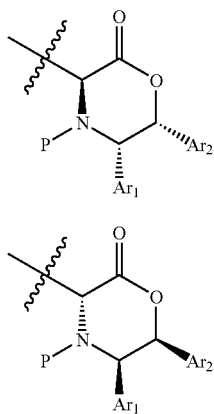

(IIIa)

(IIIb)

In certain embodiments of the compounds of formula I, wherein B has the formula III, $Ar_1$ and $Ar_2$ are phenyl which may be substituted optionally with alkyl, hydroxy, halo, amino, aminoalkyl, or alkoxy substituents. P is an amine protecting group. Any suitable amine protecting group known to those of skill in the art can be used, and for example, the amine protecting group is selected from the group consisting of fluorenylmethoxycarbonyl (Fmoc), tert-butoxycarbonyl (t-Boc), carbobenzoxy (Cbz), and carbamoyl. Preferably, the amine protecting group is Fmoc, t-Boc, or Cbz, and more preferably, Fmoc.

B of formula IV can have the following structures

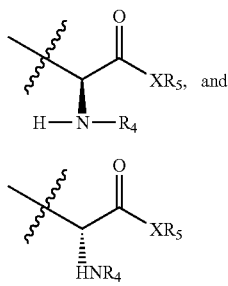

(IVa)

(IVb)

wherein X is NH or O; $R_4$ is hydrogen, $C_1$–$C_6$ alkyl, aryl, $C_1$–$C_6$ alkylaryl, and $C_1$–$C_6$ alkyl, or an amine protecting group; and $R_5$ is selected from the group consisting of hydrogen, $C_1$–$C_6$ alkyl, aryl, aryl $C_1$–$C_6$ alkyl, $C_1$–$C_6$ alkylaryl, and heteroaryl. The compound having B of formula IVa is preferred.

In some preferred embodiments, the compound of formula I has the formula IVa and X is O. $R_4$ is hydrogen in certain embodiments. In some preferred embodiments of the compounds of formula I, B has the formula IVa, X is O, and $R_4$ is an amine protecting group. Any suitable amine protecting group known to those of skill in the art can be used, and for example, the amine protecting group is selected from the group consisting of Fmoc, t-Boc, Cbz, and carbamoyl. Preferably, the amine protecting group is Fmoc, t-Boc, or Cbz, and more preferably, Fmoc.

In some embodiments of the compounds of formula I, B has the formula IVa or IVb, X is NH or O, and $R_4$ is an amine protecting group $R_5$ is hydrogen. In certain preferred embodiments of the compounds of formula I, B has the formula IVa or IVb, X is NH or O, $R_4$ is an amine protecting group $R_5$ is hydrogen, and A is a malonyl group of formula II wherein $R_1$ and $R_2$ are hydrogen. It is further preferred that $R_3$ is hydrogen.

In certain embodiments of the compound of formula I, C is hydrogen. In some embodiments of the compound of formula I, C is $C_1$–$C_6$ alkyloxycarbonyl, for example, C is t-Boc. Thus, certain embodiments of the present invention include compounds of formula I wherein B has the formula IVa or IVb, X is NH or O, $R_4$ is an amine protecting group, $R_5$ is hydrogen, A is a malonyl group of formula II wherein $R_1$ and $R_2$ are hydrogen, and C is hydrogen or $C_1$–$C_6$ alkyloxycarbonyl.

In some embodiments of the compound of formula I, C is $C_1$–$C_6$ alkylcarbonyloxy, for example, C is acetyloxy. Thus, certain embodiments of the present invention include compounds of formula I wherein B has the formula IVa or IVb, X is NH or O, $R_4$ is an amine protecting group, $R_5$ is hydrogen, A is a malonyl group of formula II wherein $R_1$ and $R_2$ are hydrogen, and C is $C_1$–$C_6$ alkyloxycarbonyl.

Preferred examples of compounds of formula I include a compound wherein A has the formula II wherein $R_1$ and $R_2$ are tert-butyl and $R_3$ is hydrogen, C is hydrogen, and B has the formula IVa wherein X is O, $R_4$ is Fmoc, and $R_5$ is hydrogen; a compound wherein A is t-butoxycarbonylmethyl, C is t-butoxycarbonyl, and B has the formula IVa wherein X is O, $R_4$ is Fmoc, and $R_5$ is hydrogen; and a compound wherein A is t-butoxycarbonylmethyl, C is acetoxy, and B has the formula IVa wherein X is O, $R_4$ is Fmoc, and $R_5$ is hydrogen.

The compounds of formula I can be prepared by processes known to those skilled in the art. The present invention provides a process for preparing compounds of formula I, particularly a compound of formula VIII. The present invention provides a process for preparing a compound of formula VIII wherein $R_2$ is alkyl and P is an amine protecting group; the process comprising:

(a) reducing the compound of formula (VII), wherein P is an amine protecting group to obtain a compound of formula IX; and (b) reacting the compound of formula IX with an amine protecting reagent to obtain the compound of formula VIII.

The present invention further provides a process for preparing a compound of formula VII, wherein $R_2$ is alkyl; the process comprising:

(a) converting a p-halotoluene to a p-tolyl-malonic acid dialkyl ester by contacting the p-halotoluene with a dialkylmalonate and a cuprous halide;

(b) halogenating the p-tolyl-malonic acid dialkyl ester to obtain a (4-halomethylphenyl)-malonic acid dialkyl ester; and (c) contacting the (4-halomethylphenyl)-malonic acid dialkyl ester with a benzyl-6-oxo-2,3-diaryl-4-morpholine to obtain the compound of formula VII.

An embodiment of the process of the present invention is schematically illustrated in FIG. 1. Thus, for example, p-iodotoluene is contacted with di-tert-butyl malonate and cuprous chloride in the presence of a base such as sodium hydride. The reaction, which produces a p-tolyl-malonic acid dialkyl ester, is carried out in a solvent, preferably a dry polar solvent, such as a solvent including dioxane and hexamethyl phosphoramide (HMPA), at a temperature of form about 80 to about 120° C., and preferably from about 90 to about 110° C. At the end, the reaction mixture is cooled to room temperature (20–25° C.), followed by quenching with an ammonium salt. The dialkyl ester is then isolated from the reaction mixture. Preferably, the reaction mixture is extracted with an extracting solvent such as ethyl acetate, washed with brine, and dried. The extracting solvent is then removed, e.g., by distillation, and the resulting dialkyl ester is purified on a chromatographic column.

The p-tolyl-malonic acid dialkyl ester prepared as above can be halogenated by known halogenating agents, e.g., N-bromosuccinimide (NBS). Thus, the p-tolyl-malonic acid dialkyl ester is combined with NBS and a peroxide in a suitable solvent such as $CCl_4$. The reaction is carried out at an elevated temperature, preferably at the reflux temperature of the solvent. The precipitates that form are removed, and the desired product is isolated from the liquid portion of the reaction mixture. The liquid portion can be extracted with a non-polar solvent, preferably repeatedly, and the combined non-polar solvent extract is dried. The resulting product, (4-bromophenyl) malonic acid dialkyl ester, is preferably purified on a chromatographic column.

The (4-bromophenyl) malonic acid dialkyl ester prepared as above can be contacted with a benzyl-6-oxo-5,6-diaryl-4-morpholine-carboxylate in the presence of a suitable base to produce a benzyl-3-[dialkyloxycarbonylmethyl)phenylmethyl]-6-oxo-5,6-diaryl-4-morpholine-carboxylate. A polar solvent such as tetrahydrofuran containing HMPA is used for carrying out the reaction. The reaction is carried out at a low temperature, preferably at about −78° C. Lithium bis(trimethylsilyl)amide is an example of a suitable base. After the reaction is complete, the reaction mixture is quenched with an ammonium salt solution. The desired product is extracted, preferably repeatedly, into a non-polar solvent such as ethyl acetate. The non-polar solvent extract is washed with water, dried, and concentrated. The product can be purified on a chromatographic column.

4-(dialkyloxycarbonylmethyl)-phenylalanine can be prepared by reducing the benzyl-3-[dialkyloxycarbonylmethyl)phenylmethyl]-6-oxo-5,6-diaryl-4-morpholine-carboxylate. The reaction can be carried out by hydrogen and a suitable catalyst, e.g., by using hydrogen and palladium black. The reduction can be carried out in a solvent such as tetrahydrofuran-ethanol mixture containing a small amount of acid such as acetic acid. The hydrogen pressure can be maintained at about 45 to about 25 psi, and the reduction can be carried out at room temperature. The resulting product can be purified by washing with an ether. The product of desired stereochemistry can be obtained by the choice of the stereochemistry of the benzyl-6-oxo-2,3-diphenyl-4-morpholine. Thus, benzyl-3-[dialkyloxycarbonylmethyl)phenylmethyl]-6-oxo-5,6-diaryl-4-morpholine-carboxylate can be obtained by choosing benzyl (2R,3S)(−)-6-oxo-2,3-diphenyl-4-morpholine.

N-Fmoc-4-(dialkyloxycarbonylmethyl)-phenylalanine can be prepared be reacting 4-(dialkyloxycarbonylmethyl)-phenylalanine with an amine protecting agent, e.g., Fmoc-OSu. A base such as sodium bicarbonate can be used to carry out the reaction. The reaction can be carried out in a solvent, e.g., a solvent containing dioxane and water, at room temperature. The reaction is carried out until completion. At the end of the reaction, the reaction mixture is cooled, preferably to 0° C., and acidified. The product is then extracted into an organic solvent, e.g., ethyl acetate, preferably repeatedly. The combined organic extract is washed with water, dried, and concentrated. The resulting crude product can be purified on a chromatographic column, e.g., a silica gel column.

The present invention further provides a conjugate comprising a conjugant covalently linked to a compound of formula I. The conjugate of the present invention can find particular use in the treatment or prophylaxis of various diseases or conditions in a mammal, preferably a human, wherein the phenylalanyl moiety of the conjugate interacts or facilitates interaction, or blocks other ligands from interacting or binding, with a domain or receptor site responsible for the onset or development of a disease or condition. Examples of such domains include the SH2 domains. Examples of such diseases or conditions include proliferative diseases such as cancer and autoimmune diseases. The conjugates also find use in diagnosis, assay, screening, and testing.

The conjugant can be any suitable material that provides a conjugate as described above. The conjugant can be an amino acid or nucleic acid, for example, a natural or synthetic peptide or nucleotide. The conjugant can be a natural or synthetic polymer, for example, carbohydrate polymers. A preferred conjugate is one that contains an amino acid, for example, the conjugates of formula X below.

Accordingly, the present invention provides a compound of the formula:

$$W—Y—(AA)_n—Z \qquad\qquad (X)$$

wherein n is 0 to 15;

Y is a phenylalanyl radical having a phenyl ring, an amine end, and a carboxyl end, the phenyl ring having one or more substituents selected from the group consisting of hydroxyl, carboxyl, formyl, carboxyalkyl, carboxyalkyloxy, dicarboxyalkyl, dicarboxyalkyloxy, dicarboxyhaloalkyl, dicarboxyhaloalkyloxy, and phosphonoalkyl, phosphonohaloalkyl, wherein the alkyl portion of the substituents may be unsubstituted or substituted with a substituent selected from the group consisting of halo, hydroxy, carboxyl, amino, aminoalkyl, alkyl, alkoxy, and keto;

W is a moiety attached to the nitrogen of Y and is selected from the group consisting of alkylcarbonyl, oxalkyl, alkylaminooxalyl, arylaminooxalyl, aryl alkylaminooxalyl, alkoxyoxalkyl, carboxyalkyl carbonyl, heterocycyl carbonyl, heterocyclylalkyl carbonyl, arylalkyl heterocyclylalkyl carbonyl, aryloxycarbonyl, and arylalkoxycarbonyl, wherein the aryl and alkyl portions of the substituents may be unsubstituted or substituted with a substituent selected from the group consisting of halo, hydroxy, carboxyl, amino, aminoalkyl, alkyl, alkoxy, and keto; and the heterocyclyl portion of W contains at least 4 hetero atoms selected from the group consisting of O, N, and S;

AA is an amino acid, the amine end of which is attached to the carboxyl end of Y; and Z is an arylalkylamino or arylheterocyclyl alkylamino; or a salt thereof;

with the proviso that W is not arylalkylamino when the phenyl ring of phenylalanyl contains a phosphonoalkyl or phosphonohaloalkyl substituent at a position para to the alkylamino group and the ortho and meta positions are unsubstituted.

The alkyl portion of the various groups described above can have any suitable number of carbon atoms, e.g., from 1 to about 12 carbon atoms, preferably from 1 to 6 carbon atoms, and more preferably from 1 to 4 carbon atoms. The aryl portion of the various groups described can have any number of aromatic rings, e.g., from 1 to 3 six rings, preferably 1 to 2 rings, and more preferably 1 ring. Thus, for example, the present invention provides a compound of formula XI wherein Y is a phenylalanyl radical having a phenyl ring, an amine end, and a carboxyl end, the phenyl ring having one or more substituents, selected from the group consisting of hydroxyl, carboxyl, formyl, carboxy $C_1$–$C_6$ alkyl, carboxy $C_1$–$C_6$ alkyloxy, dicarboxy $C_1$–$C_6$ alkyl, dicarboxy $C_1$–$C_6$ alkoxy, dicarboxylhalo $C_1$–$C_6$ alkyl, dicarboxyhalo $C_1$–$C_6$ alkyloxy, and phosphono, $C_1$–$C_6$ alkyl, phosphonohalo $C_1$–$C_6$ alkyl, wherein the alkyl portion of the substituents may be unsubstituted or substituted with a substituent selected from the group consisting of halo, hydroxy, carboxyl, amino, amino $C_1$–$C_6$ alkyl, $C_1$–$C_8$ alkyl, $C_1$–$C_6$ alkoxy, and keto;

W is a moiety attached to the nitrogen of Y and is selected from the group consisting of $C_1$–$C_6$ alkylcarbonyl, oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl, aryl $C_1$–$C_6$ alkyl heterocyclyl $C_1$–$C_6$ alkyl carbonyl, aryloxycarbonyl, and aryl $C_1$–$C_6$ alkoxycarbonyl, wherein the aryl and alkyl portions of the substituents may be unsubstituted or substituted with a substituent selected from the group consisting of halo, hydroxy, carboxyl, amino, amino $C_1$–$C_6$ alkyl, $C_1$–$C_6$ alkyl, $C_1$–$C_6$ alkoxy, and keto; and the heterocyclyl portion of W contains at least 4 hetero atoms selected from the group consisting of O, N, and S;

AA is an amino acid, the amine end of which is attached to the carboxyl end of Y; and Z is an aryl $C_1$–$C_6$ alkylamino or arylheterocyclyl $C_1$–$C_6$ alkylamino;

or a salt thereof. The compounds can be in D, L, or a mixed form thereof.

Preferred compounds of formula X include those wherein Y is of formula XI:

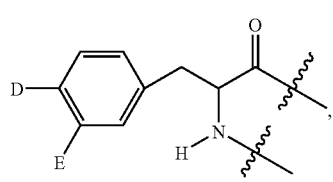

(XI)

wherein D has the formula XII, XIII, or XIV:

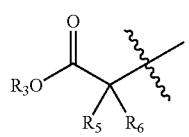

(XII)

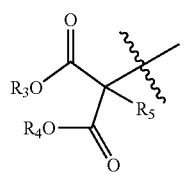

(XIII)

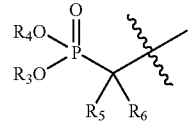

(XIV)

wherein $R_3$ and $R_4$ may be the same or different and are selected from the group consisting of hydrogen, $C_1$–$C_6$ alkyl, aryl, aryl $C_1$–$C_6$ alkyl, $C_1$–$C_6$ alkaryl, and heteroaryl; and $R_5$ and $R_6$ may be the same or different and are selected from the group consisting of hydrogen, halo, hydroxy, amino, and $C_1$–$C_6$ alkoxy; and E is selected from the group consisting of hydrogen, hydroxy, $C_1$–$C_6$ alkyl, $C_1$–$C_6$ alkylcarbonyl, carboxyl, and $C_1$–$C_6$ alkylcarbonyl $C_1$–$C_6$ alkyl.

Particular examples of compounds of the present invention include compounds of formula X wherein D has the formula XII, XII, or XIII, and E is hydrogen, hydroxy, or carboxyl. In some embodiments, $R_3$, $R_4$, $R_5$, and $R_6$ are hydrogen. Certain embodiments include compounds wherein D has the formula XII, E is hydroxy or carboxyl, and $R_3$, $R_5$, and $R_6$ are hydrogen; and D has the formula XIII, E is hydrogen, $R_3$ and $R_4$ are hydrogen, and $R_5$ is hydrogen, hydroxy, alkyloxy, halo, keto, or alkyl, and preferably $R_5$ is hydrogen.

In certain embodiments, W is $C_1$–$C_6$ alkylcarbonyl, preferably $C_1$–$C_3$ alkylcarbonyl, for example, acetyl. In some embodiments, W is oxalyl or carboxymethylcarbonyl. In some other embodiments, W is tetrazolylcarbonyl, and preferably tetrazolylmethylcarbonyl. W can be an arylmethyloxycarbonyl, preferably, an aminophenylmethyloxycarbonyl, and more preferably 3-aminophenyl-1-methyloxycarbonyl in some embodiments. W can also be an aryloxycarbonyl. Preferably a naphthyloxycarbonyl, and more preferably an aminonaphthyloxycarbonyl. An example of an aminonaphthyloxycarbonyl is 6-amino-1-naphthyloxycarbonyl.

The present invention also provides compounds of formula X wherein W is an arylmethyltetrazolylmetylcarbonyl, e.g., a phenylmethyltetrazolylmethylcarbonyl. The present invention further provides a compounds of formula X wherein W is an alkoxyphenylmethyltetrazolylmethylcarbonyl, e.g., a methoxyphenylmethyltetrazolylmethylcarbonyl.

In embodiments of the compounds of formula X wherein Z is an aryl alkylamino, the aryl portion of Z has the formula:

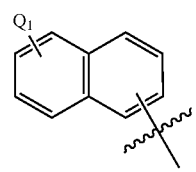

wherein $Q_1$ is hydrogen or a substituent selected from the group consisting of hydroxyl, halo, $C_1$–$C_6$ alkyl, $C_1$–$C_6$ alkoxy, amino, and $C_1$–$C_6$ acylamino.

The aryl portion of Z is preferably attached to the alkylamino portion of Z at the aryl 1- and 2-position. A preferred compound of formula XI is one wherein $Q_1$ is hydrogen or methyl. A preferred compound of formula XI is one wherein Z is naphthylpropylamino.

In embodiments of the compounds of formula X wherein Z is aryl heterocyclyl alkylamino, the heterocyclyl portion of Z has the formula:

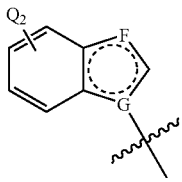

wherein $Q_2$ is hydrogen or a substituted selected from the group consisting of hydroxyl, halo, $C_1$–$C_6$ alkyl, $C_1$–$C_6$ alkoxy, amino, and $C_1$–$C_6$ acylamino, and F and G are independently selected from the group consisting of C, N, O, and S. A preferred F is C, and a preferred G is N. A preferred compound of formula X is one wherein $Q_2$ is is hydrogen or methyl.

The number of amino acid segments or units in the compounds of formula X can be from 0 to 15. Compounds having smaller n values are preferred. For example, compounds wherein n is 1–10 are preferred; compounds wherein n is 1–3 are more preferred; and compounds wherein n is 2 are further preferred.

The compounds of formula X can include any suitable amino acid. For example, the amino acid can be selected from the group comprising, preferably consisting of, glycine, alanine, valine, norvaline, leucine, isoleucine, norleuncine, α-amino n-decanoic acid, serine, homoserine, threonine, methionine, cysteine, S-acetylaminomethyl-cysteine, proline, trans-3- and trans-4-hydroxyproline, phenylalanine, tyrosine, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, 4-aminocyclohexylglycine, 4-acylaminocyclhexylglycine, tryptophan, indoline-2-carboxylic acid, 1,2,3,4-tetrahydroisoquinonline-3-carboxylic acid, aspartic acid, asparagine, aminomalonic acid, aminomalonic acid monoamide, glutamic acid, glutamine, histidine, arginine, lysine, N'-benzyl-N'-methyl-lysine, N',N'-dibenzyl-lysine, 6-hydroxylysine, ornithine, α-aminocyclopentance carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

Preferably, the amino acid is selected from the group consisting of leucine, iso-leucine, norieucine, cyclohexylalnine, cyclohexylglycine, 4-aminocyclohexylglycine, 4-acylaminocyclhexylglycine, aspartic acid, asparagine, glutamic acid, and glutamine.

It is further preferred that the compound of formula X includes a first amino acid ($AA_1$) attached to the phenylalanine moiety (Y) and asparagine attached to $AA_2$, wherein said $AA_1$ is selected from the group consisting of cyclohexylglycine, aspartic acid, glutamic acid, 4-aminocyclohexylglycine, 4-acylaminocyclohexylglycine, leucine, and isoleucine. A preferred compound of formula X is one wherein $AA_1$ is cyclohexylglycine.

Figure 2:
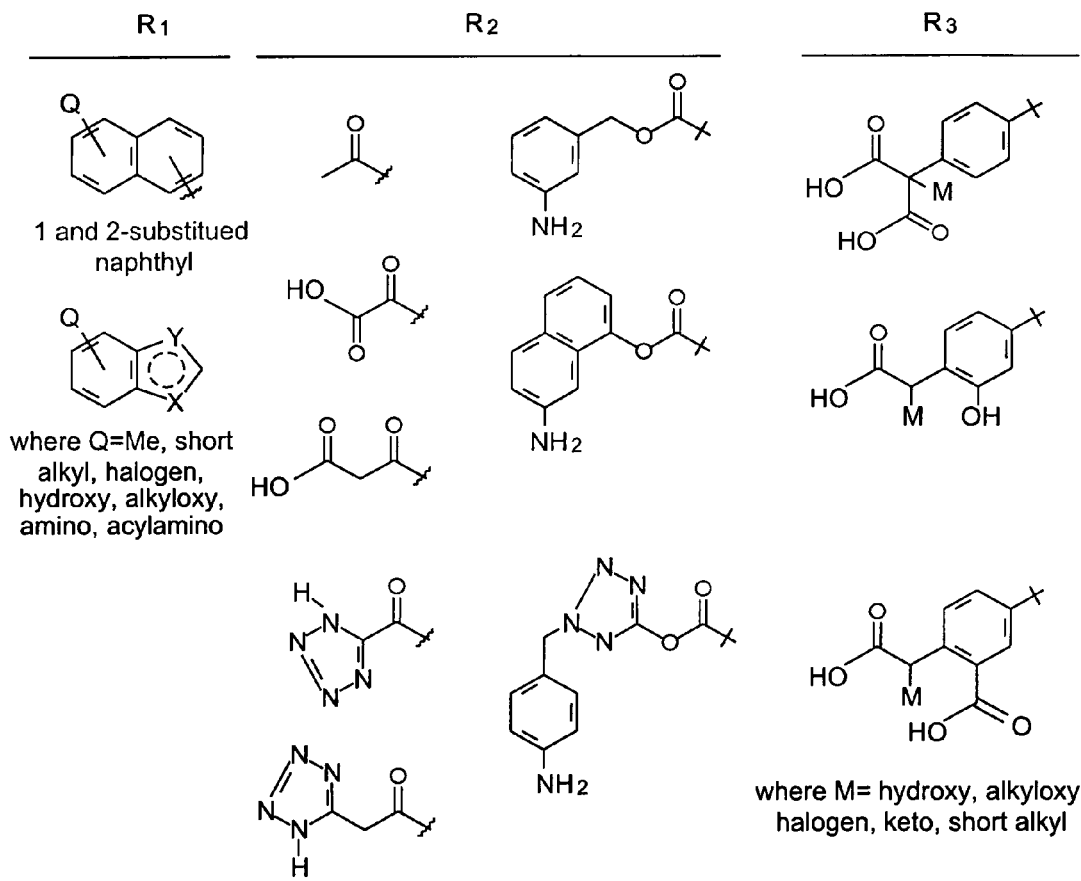
FIG. 2 depicts some embodiments of the compounds of formula X in accordance with the present invention.

Further examples of compounds of formula X are set forth in FIG. 2. The compounds of formula I can be prepared by methods known to those skilled in the art. For example, the compounds can be prepared by the solid phase or solution phase peptide synthesis methods. Thus, the compounds can be prepared by reacting an amino acid or a peptide with the precursors of the present invention. Some embodiments of the synthetic method are illustrated in the Examples.

The present invention further provides a composition comprising a pharmaceutically acceptable carrier and an effective (e.g., therapeutically or prophylactically effective) amount of at least one of the compounds set forth above, particularly a compound of formula X. The present invention further provides a method of inhibiting an SH2 domain from binding with a phosphoprotein comprising contacting a sample or substance containing an SH2 domain with a compound of formula X.

The present invention discloses the use of a compound of formula X in the manufacture of a medicament for the treatment of a condition that responds to the inhibition of phosphoprotein binding to an SH2 domain of a mammal. The present invention further teaches the use of a compound of formula X in medicine. The compounds of formula X find use as a Grb2-SH2 domain inhibitor.

The pharmaceutically acceptable (e.g., pharmacologically acceptable) carriers described herein, for example, vehicles, adjuvants, excipients, or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can comprise (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, iospropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animals, vegetable, or synthetic oils. Specific examples of oils include peanut, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic, acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5 to about 25% by eight of the active ingredient in solution. Suitable preservatives and buffers can be used in such formulations. In order to minimize or eliminate irritation at the site of injection, such compositions may contain one or more nonionic surfactants. The quantity of surfactant in such formulations typically ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chaimers, etcs., pages 238–250 (1982), and *ASHP Handbook on Injectable Drugs*, Toissel, 4th ed., pages 622–630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of responses. Typically the dosages range from about 0.001 to about 1000 mg/kg body weight of the animal being treated/day. Preferred dosages range from about 0.01 to about 10 mg/kg body weight/day, and further preferred dosages range from about 0.01 to about 1 mg/kg body weight/day.

The compounds of formula X have the advantage that they are stable to or in presence of enzymes encountered during in vivo use. The compounds of formula X can find use in in vitro and in vivo applications. For example, the compounds can find use as molecular probes as well as in assays to identify, human breast cancer are dependent upon activation of the Ras signaling pathways through activation of growth factor receptor as the means to achieve continuous cellular proliferation. For example, the cancer may involve overexpression of Her-2/neu. The cancer can be mediated through BCR-Abl or the expression of erbB-2 receptor. In cells transformed by p185 erbB-2 overexpression, therapeutic agents affecting Grb2 function at its SH2 domain may interrupt the flow of signal transduction to the ras pathway and thus result in reversal of the cancer phenotype.

The therapeutic treatment can include a chemotherapy, a radiation therapy, and/or a biological therapy. Examples of chemotherapy includes the use of cancer treatment agents such as alkylating agents, hormonal agents, antimetabolites, natural products, and miscellaneous agents. Particular examples of cancer treatment agents include paclitaxel, 5-fluoruracil, and doxorubicin. Examples of biological therapy includes the use of a protein such as an antibody (monoclonal or polyclonal) or a recombinant protein. An example of an antibody is herceptin, which is targeted for inhibiting the erbB-2 receptor. In embodiments, the enhancement of the therapeutic effect comprises blocking of a cell survival factor in the mammal and/or triggering, e.g., enhancing or speeding up, of cell apoptosis. The treatment can be carried out in vivo and/or in vitro.

The present invention further provides a method of inhibiting the MAP kinase activity in a mammal. MAP kinases function in a protein kinase cascade that plays a critical role in the regulation of cell growth and differentiation. MAP kinases are activated by a variety of signals including growth factors, cytokines and hormones through Grb2 and other signaling proteins. For example, the state of threonine and tyrosine phosphorylation of cellular MAP kinase is determined in MDA-453 cells treated with growth factor heregulin (HRG) using a polyclonal antibody specifically recognizing the phosphorylated threonine and tyrosine residues of MAP kinase. A dose-dependent inhibition of MAP kinase activity is observed in MDA-MD-453 cells. The $IC_{50}$ value of MAP kinase inhibition is 12.5 μM for compound 126, which is in consistent with cell growth inhibition.

The Grb2 SH2 binding inhibitors are effective in inhibiting the association or binding of Grb2 with activated receptor PTKs. Interaction of native Grb2 protein with phosphotyrosinylated proteins including receptor PTKs can be monitored by immunoprecipitating Grb2 and detecting the amount of phosphotyrosinylated proteins which are coprecipitated using anti-phosphotyrosine Western Blotting. For example, with compounds 126, MDA-MB-453, BT-474 and SKBr3, show heavily phosphorylated proteins including a band corresponding to the overexpressed p185erbB-2. MDA-MB-468 and MDA-MB-231 cells show moderate to low level of phosphorylated protein at 170 kD corresponding to the overexpression of the EGFR. The NIH/3T3 fibroblast engineered to express erbB-2 are also show growth inhibition.

The compounds of the present invention exert a cytostatic effect. For example, compound 126 inhibits MDA-MB-453 cells that have Grb2 activity through erbB-2 receptor overexpression. Tumor growth inhibition is also seen in MDA-453/M1 breast cancer xenografts in athymic mice with compound 126. The compounds of the present invention are free or substantially free of toxicity. For example, in female nude mice injected with human breast cancer cell line BT-474 cells, no systemic toxicity is observed with compound 126.

The following examples further illustrate the present invention but, of course, should not be construed as in any way limiting its scope.

EXAMPLE 1

This Example illustrates a method of preparing and characterizing certain compounds of formula I. The synthetic procedure is schematically illustrated in FIG. 1.

p-Tolyl-malonic acid di-tert-butyl ester (2). To the suspension of sodium hydride (60%, 1.2 g, 30 mmol) in 50 ml of anhydrous dioxane containing 3.5 ml of HMPA were added di-tert-butyl malonate (6.488 g, 30 mmol) and p-iodotoluene (1), the mixture was stirred at room temperature for 1 hour. To the resulting solution was added copper (I) bromide (5.163 g, 36 mmol, 1.2 equivalents), the mixture was heated at refluxing temperature. Then the reaction mixture was cooled to room temperature, 30 ml of saturated aqueous ammonium chloride solution was added to quench the reaction, and the product was extracted with ethyl acetate (50 ml×3), washed with brine, dried over sodium sulfate. The solvent was evaporated, and the oily residue obtained was purified by chromatography to give p-tolyl-malonic acid di-tert-butyl ester 5.072 g (yield 55.2%) was a white solid. $^1$H NMR (CDCl$_3$) δ: 7.275 (2H, d, J=8.06 Hz), 7.161 (2H, d, J=8.05 Hz), 4.397 (1H, s), 2.344 (3H, s), 1.471 (18H, s) ppm. FABMS ($^+$Ve), m/z 307 [MH$^+$], 251 [MH$^+$—C$_4$H$_8$], 195 [MH$^+$—2C$_4$H$_8$]. Anal. calcd. for C$_{18}$H$_{26}$O$_4$: C, 70.6; H, 8.6. Found: C, 70.34; H, 8.62.

(4-Bromomethylphenyl)-malonic acid di-tert-butyl ester (3). p-Tolyl-malonic acid di-tert-butyl ester (5.695 g, 16.6 mmol) was dissolved in 80 ml of CCl$_4$. To the solution was added N-bromosuccinimide (3.309 g, 16.6 mmol, 1 equivalents) and benzoyl peroxide (220 mg), the reaction mixture was refluxed under argon overnight; the reaction mixture was then cooled to room temperature, and the precipitate that had formed was filtered and washed with hexanes. The combined organic portions was dried, and the residue obtained was purified by chromatography to give (4-bromomethylphenyl)-malonic acid di-tert-butyl ester 4.2559 g (59.5% yield) as white solid. $^1$H NMR (CDCl$_3$) δ: 7.379 (4H, s), 4.493 (2H, s), 4.435 (1H, s), 1.473 (18H, s) ppm. FABMS ($^+$Ve), m/z 387 [MH$^+$, $^{81}$Br], 385 [MH$^+$, $^{79}$Br], 331 [MH$^+$—C$_4$H$_8$, $^{81}$Br], 329 [MH$^+$—C$_4$H$_8$. $^{79}$Br], 275 [MH$^+$—2C$_4$H$_8$, $^{81}$Br], 273 [MH$^+$—2C$_4$H$_8$, $^{79}$Br]. Anal. calcd. for C$_{18}$H$_{25}$BrO$_4$: C, 56.1; H,6.5; Br, 20.7. Found: C, 55.52; H, 6.38; Br, 21.85.

Benzyl (3S,5S,6R)-3-[4-(di-tert-butoxycarbonylmethyl) phenylmethyl]-(−)-6-oxo-5,6-diphenyl-4-morpholine-carboxylate (4). To a solution of benzyl (2R,3S)-(−)-6-oxo-2,3-diphenyl-4-morpholine-carboxylate (2.688 g, 6.94 mmol) in anhydrous tetrahydrofuran (60 ml) and HMPA (4.6 ml) cooled to −78° C. under at argon atmosphere was added lithium bis(trimethylsilyl)amide (1.0M solution in hexanes, 7.29 ml, 7.29 mmol, 1.05 equivalents). the reaction mixture was stirred at −78° C. for 1 hour. A solution of 2-(4-bromomethylphenyl)-malonic acid di-tert-butyl ester (2.6755 g, 6.94 mmol) in THF was added slowly at −78° C. via a syringe, and the mixture was first stirred at −78° C. for 2 hours and then the temperature was raised to room temperature, and the mixture was stirred overnight. The mixture was then quenched with aqueous NH$_4$Cl (10 ml) and diluted with 35 ml of water. The mixture was extracted with ethyl acetate repeatedly, and the combined organic extracts were washed successively with water, aqueous NH$_4$Cl, and brine, dried over Na$_2$SO$_4$. Concentration and purification by silica gel chromatography (hexanes-ethyl acetate, from 6:1 to 3:1) gave benzyl (3S,5S,6R)-3-[4-(di-tert-butoxycarbonyl-methyl)phenylmethyl]-(−)-6-oxo-5,6-diphenyl-4-morpholine carboxylate as a white solid (1.88 g, 39.2% yield). $^1$H NMR (CDCl$_3$) (two conformers were observed in a ratio of 5:7 at 23° C.) δ: 7.462~7.354 (3H, m, overlapping), 7.285~7.046 (10 H, m, overlapping), 6.914~6.720 (4H, m, overlapping), 6.546 (2H, m, overlapping); major conformer: 5.374 (1H, d, J=2.69 Hz, —PhCHOOC—), 5.172~5.045 (3H, m, overlapping, —OOCCH-N, —PhCHN—, OCH$_2$Ph), 4.960 (1H, d, J=13.19 Hz, OCH$_2$Ph), 4.655 [1H, s, (tBuOOC)$_2$CH—], 3.606~3.516 (1H, dd, J=8.06, 13.43 Hz, —CH$_2$—CHNCOO), 3.455~3.358 (1H, m, —CH$_2$—CHNCOO), 1.420 (9H, s), 1.394 (9H, s) ppm; minor conformer: 5.708 (1H, J, J=2.20 Hz, —PhCHOOC—), 5.172~5.045 (4H, m, overlapping, —OOCCH-N, —PhCHN—, OCH$_2$Ph), 4.626 [1H, s, (tBuOOC)$_2$CH—], 3.606~3.350 (2H, m, overlapping, —CH$_2$—CHNCOO), 1.421 (9H, s) ppm; FABMS ($^+$ve), m/z 580.5 [MH$^+$—2 C$_4$H$_8$], 536.5 [MH$^+$—2C$_4$H$_8$—CO$_2$], 492.5 [MH$^+$—2C$_4$H$_8$—2CO$_2$]. Anal. calcd. for C$_{42}$H$_{45}$NO$_8$: C, 72.9; H, 6.6; N, 2.0. Found: C, 72.62; H, 6.69; N, 1.85.

4-(Di-tert-butoxycarbonyl-methyl)-L-phenylalanine (5). Benzyl (3S,5S,6R)-3-[4-(di-tert-butoxycarbonyl-methyl) phenylmethyl]-(−)-6-oxo-5,6-diphenyl-4-morpholine carboxylate (1.78 g, 2.57 mmol) was dissolved in THF-EtOH mixture (1:1, 15 ml, 2 drops of AcOH was added to promote the reaction) and hydrogenated over Pd black (200 mg) under high pressure (45 psi ~20 psi or 310 kPa to about 138 kPa) at room temperature (24 hours). The mixture was filtered off and the solid was washed with MeOH. The combined organics were concentrated to give a white sticky solid. The solid was washed thoroughly with ether to remove 1,2-diphenylethane and dried under vacuum to provide 4-(di-tert-butoxycarbonyl-methyl)-L-phenylalanine as a white powder (842 mg, 86.3%), $^1$H NMR (DMSO) δ: 7.251 (4H, s), 4.590 (1H, s), 3.422~3.316 (3H, m, OOCCH-N, —NH$_2$), 3.17~3.01 (1H, m, —CH$_2$—CHNCOO), 2.943~2.785 (1H, m, —CH$_2$—CHNCO), 1.416 (18H, s) ppm; FABMS ($^+$Ve), m/z 268 [MH$^+$—2 C$_4$H$_8$], Anal. calcd. for C$_{20}$H$_{29}$NO$_6$: C, 63.3; H, 7.7; N, 3.7. Found: C, 63.26; H, 7.82; N, 3.52.

N-Fm c-4-(di-tert-butoxycarbonyl-methyl)-L-phenylalanin (6). A mixture of 4-(di-tert-butoxycarbonyl-methyl)-L-phenylalanine (818 mg, 2.16 mmol), Fmoc-OSu (727 mg, 2.16 mmol) and NaHCO$_3$ (906 mg, 10.8 mmol, 5 equivalents) in 48 ml of dioxane-water (1:1) was stirred at room temperature overnight. The reaction mixture was then cooled to 0° C. and acidified with 180 ml of 0.2 M HCl. The reaction product was extracted with ethyl acetate (30 ml×3), and the combined organic extracts were washed with brine, dried (Na$_2$SO$_4$) and concentrated. The crude product was purified by silica gel chromatography (CDCl$_3$-EtOAc-MeOH) to provide N-Fmoc-4-(di-tert-butoxycarbonyl-methyl)-L-phenylalanine as a white solid (650 mg, 50.7%). $^1$H NMR (DCMSO) δ: 12.704 (1H, s, br), 7.786 (2H, d, J=7.32 Hz), 7.760 (1H, d, J=8.54 Hz), 7.658 (2H, t, J=7.81 Hz), 7.435~7.200 (4H, m) 7.254 (4H, s), 4.586 (1H, s), 4.274~4.081 (4H, m), 3.111~3.040 (1H, dd, J=4.40, 13.67 Hz), 2.913~2.815 (1H, dd, J=10.75, 13.92 Hz), 1.390 (1H, s), 1.380 (1H, s). FABMS ($^+$Ve), m/z 602 [MH$^+$], 546 [MH$^+$—C$_4$H$_8$], 490 [MH$^+$—2 C$_4$H$_8$]. Anal. calcd. for C$_{20}$H$_{29}$NO$_6$: C, 66.90; H, 6.5; N, 2.3. Found: C, 90.40; H, 6.67; N, 2.24.

EXAMPLE 2

This Example illustrates a method of preparing embodiments of formula X. The reactions are schematically depicted in FIGS. 4–14.

Compound 8. To the solution of compound 7 (45.5 mg, 0.1 mmol) in anhydrous DMF (2 ml) was added an active ester solution formed by reacting N-Fmoc-4-(di-tert-butoxycarbonyl-methyl)-L-phenylalanine (60.1 mg, 0.1 mmol), HOBt, H$_2$O (13.5 mg, 0.1 mmol) and DIPCDI (15.6 μl, 0.1 mmol) in anhydrous DMF (2 ml) at room temperature (10 min.). The reaction mixture was then stirred at room temperature overnight. The solvent was removed under high vacuum and the residue obtained was purified by silica gel chromatography (CHCl$_3$-EtoAc-MeOH mixture) to provide the desired product, compound 8, as a white foam (100% yield). $^1$H NMR (CDCl$_3$) δ: 8.01 (2H, m), 7.81~7.71 (6H, m), 7.50~6.95 (12H, m), 6.58 (1H, s), 5.56 (3H, m), 4.69 (1H, m), 4.55~4.40 (1H, m), 4.40 (1H, s) 4.31 (2H, d, J=6.84 Hz), 4.09 (1H), m), 3.34 (1H, m), 3.12~2.88 (5 H, m), 2.63 (1H, dd, J=4.4, 15.1 Hz), 2.05~1.11 (12H, m), 1.46 (18H, s) ppm. FABMS ($^+$Ve), m/z 1009 [MH$^+$]. Compound 9. To the solution of compound 8 (0.05 mmol) in anhydrous acetonitrile (2 ml) was added piperidine (40 μl, 0.4 mmol, 8 equivalents) and the solution was stirred at room temperature for 3 hr. At the end, the solvent and the excess piperidine were removed under high vacuum. The residue obtained was dissolved in anhydrous DMF (2 ml). The resulting solution was added diisopropylenthylamine (13 μl, 0.075 mmol, 1.5 equivalents) followed by the addition of tert-butyl oxalyl chloride (0.5 μl, 0.075 mmol, 1.5 equivalents). The solution was stirred at room temperature overnight. The mixture was concentrated and purified by on silica gel chromatography (CHCl$_3$-EtOAc-MeOH mixture) provide product 22.8 mg (50% yield) as a white foam. $^1$H NMR (CDCl$_3$) δ: 8.02 (2H, m), 7.81~7.21 (13H, m), 6.69 (1H, s), 6.38 (1H, s), 4.67 (2H, m), 4.40 (1H, s), 3.43~2.88 (7 H, m), 2.56 (1H, dd, J=4.88, 14.89 Hz), 2.05~0.94 (12H, m), 1.464 (18H, s), 1.457 (9H, s) ppm. FABMS ($^+$Ve), m/z 914 [MH$^+$], HR-FABMS calcd for C$_{50}$H$_{67}$N$_5$O$_{11}$ m/z 913.4837 (M+), 914.4915 (MH+), found 913.4837, 914.4915.

Compound 10. To the solution of compound 8 (0.05 mmol) in anhydrous acetonitrile (2 ml) was added piperidine (40 μl, 0.4 mmol, 8 equivalents) and the solution was stirred at room temperature for 3 hr. At the end, the solvent and the excess piperidine were removed under high vacuum. The residue was taken up in anhydrous acetonitrile (3.0 ml) and treated with N-acetylimidazole (55 mg, 0,5 mmol, 10 equivalents). The solution was stirred at room temperature overnight. The solvent was removed and the residue was purified by on silica gel chromatography (CHCl$_3$-EtOAc-MeOH mixture) to provide product 38.9 mg of product (94% yield) as white foam. $^1$H NMR (CDCl$_3$) δ: 8.03 (2H, m), 7.81 (1H, m), 7.63 (3H, m), 7.46~7.05 (9H, m), 6.65 (2H, m), 4.67 (2H, m), 4.40 (1H, s), 3.34 (2H, m), 3.12~2.89 (5 H, m), 2.55 (1H, dd, J=4.60, 15.1 Hz), 1.806 (3H, s) 2.04~1.15 (12H, m), 1.46 (18H, s) ppm, FABMS ($^+$Ve), m/z 828 [MH$^+$], 772 [MH$^+$—C$_4$H$_8$], HR-FABMS calcd for C$_{46}$H$_{61}$N$_5$O$_9$ m/z 827.4469 (M+), 828.4548(MH+), found 827.4469, 828.4548.

Compound 11. A solution of compound 10 (22.3 mg, 0.0244 mmol) in TFA-H$_2$O-Triethylsilane (1.85 ml–0.1 ml–50 μl) was stirred at room temperature for 1 hr, then the solvents were evaporated under high vacuum. 5 ml of water were added and the mixture was taken to dryness again to remove the remaining TFA. This procedure was repeated two times. The crude products obtained were obtained in MeCN: H$_2$O (1:1, plus 0.1% TFA, 6 ml), filtered and purified by HPLC, using an Advantage C$_{18}$ column (250 mm×20 mm dia.) with a flow rate: 10 ml/min and a linear gradient from 5% B to 100% B over 40 min.; solvent A: 0.1% aqueous TFA; solvent B: 0.1% TFA in MeCN.

Compound 11 was obtained as a white solid (9.4 mg, 52%). $^1$H NMR (DMSO) δ: 8.82 (1H, s), 8.08 (1H, m), 8.00 (1H, d, J=7.33 Hz), 7.89 (1H, m), 7.74 (1H, m), 7.53~7.20 (10Hm, m), 6.92 (1H, s), 4.73 (1H, m), 4.60 (1H, s), 4.36 (1H, m), 3.25~2.93 (6H, m), 2.69 (1H, dd, J=6.75, 15.4 Hz), 2.52 (1H, m), 2.08~1.12 (12H, M) ppm. FABMS ($^+$Ve), m/z 744 [M-H], 700 [M-H- CO$_2$], HR-FABMS calcd for C$_{38}$H$_{43}$N$_5$O$_{11}$ m/z 745.2959 (M), 744.2881 (M-H), found 745.2959, 744.2881.

Compound 12. A solution of 10 (38.4 mg, 0.047 mmol) in TFA-H$_2$O-Triethylsilane (1.85 ml–0.01 ml–50 μl) was stirred at room temperature for 1 hr. The solvents were evaporated under high vacuum. 5 ml of water were added and the mixture was taken to dryness again to remove the remained TFA. This procedure was repeated twice. The crude product obtained was dissolved in MeCN : H$_2$O (1:1, plus 0.1% TFA, 10 ml), filtered and purified by HPLC, using an Advantage C$_{18}$ column (250 mm×20 mm dia.) with a flow rate: 10 ml/min and a linear gradient from 5% B to 100% B over 40 min; solvent A: 0.1% aqueous TFA; solvent B: 0.1% TFA in MeCN. Compound 12 was obtained as a white solid (24.5 mg, 73%). $^1$H NMR (DMSO) δ: 8.25 (2H, m), 8.08 (1H, m), 7.99 (1H, m), 7.90 (1H, m), 7.74 (1H, m0, 7.51~7.18 (10H, m), 6.90 (1H, s), 4.65 (1H, m), 4.60 (1H, s), 4.36 (1H, m), 3.35~2.98 (5H, m), 2.82~2.56 (3H, m), 1.78 (3H, s), 2.08~1.12 (12H, m) ppm, FABMS ($^-$Ve), m/z 714 [M-H], 670 [M-H-CO$_2$], 626 [M-H-2CO$_2$], HR-FABMS calcd for C$_{38}$H$_{45}$N$_5$O$_9$ m/z 715.3217 (M), 714.3139 (M-H), found 745.2959, 744.2881.

Compound 13. To the solution of compound 7 (63.6 mg, 0.14 mmol) in anhydrous DMF (2 ml) was added an active ester solution formed by N-Fmoc-[3-acetoxyl-4-(tert-butoxycarbonyl)methyl]-L-phenylalanine (78.3 mg, 0.14 mmol), HOBt.H$_2$O (18.9 mg, 0.14 mmol) and DIPCDI (21.8 µl, 0.14 mmol) in anhydrous DMF (2 ml) at room temperature (10 min.). The combined reaction mixture was then stirred at room temperature overnight. The solvent was removed under high vacuum and the residue obtained was purified by silica gel chromatography (CHCl$_3$-EtOAc-MeOH mixture) to compound 13 (123.7 mg, 91.4% yield), as a white foam. $^1$H NMR (CDCl$_3$) δ; 8.03 (2H, m), 7.82~7.23 (17 H, m), 7.17 (1H, d, J=7.81 Hz), 6.95 (2H, m), 6.79 (1H, s), 6.26 (1H, s), 4.69 (1H, m), 4.46~4.34 (3H, m), 4.14 (1H, m), 3.42 (2H, s), 3.41~3.32 (2H, m), 3.14~2.94 (4H, m), 2.64~2.45 (2H, m), 2.27 (3H, s), 2.06~1.11 (12H, m) ppm, 1.42 (9H, s). FABMS ($^+$Ve), m/z 966 [MH$^+$], 949 [MH$^+$-NH$_3$].

Compound 14. To the solution of compound 13 (61.4 mg, 0.064 mmol) in anhydrous acetonitrile (2.5 ml) was added piperidine (50 µl, 0.51 mmol, 8 equivalents) and the solution was stirred at room temperature for 3 hr. The solvent and the excess piperidine were removed under high vacuum. The residue obtained was dissolved in anhydrous DMF (2 ml), the solution was added diisopropylenthylamine (22 µl, 0.126 mmol, 2 equivalents) followed by the addition of tert-butyl oxalyl chloride (16 µl, 0.126 mmol, 2 equivalents). The solution was stirred at room temperature overnight. The solution was concentrated and purified by silica gel chromatography (CHCl$_3$-EtOAc-MeOH) mixture) to provide compound 14, 51 mg (92% yield) as a white foam. $^1$H NMR (CDCl$_3$) δ: 8.04~7.00 (12H, m), 6.79 (1H, s), 6.70 (1H, d, J=1.22 Hz), 6.46 (2H, m), 4.80~4.60 (2H, m), 3.53 (2H, s), 3.45~2.76 (7H, m), 2.56 (1H, dd, J=4.88, 15.13 Hz), 2.28 (3H, s), 2.18~1.15 (12H, m), 1.50 (9H, s), 1.46 (9H, s). FABMS ($^+$Ve), m/z 872 [MH$^+$].

Compound 15. To a solution of compound 13 (61.4 mg, 0.064 mmol) in anhydrous acetonitrile (2.5 ml) was added piperidine (50 µl, 0.51 mmol, 8 equivalents) and the solution was stirred at room temperature for 3 hr. The solvent and the excess piperidine were removed under high vacuum. The residue was taken up in anhydrous acetonitrile (3.0 ml) and treated with N-acetylimidazole (69.3 mg, 0.63 mmol, 10 equivalents). The solution was stirred at room temperature overnight. The solvent was removed under vacuum at 30° C. and the residue was purified by silica gel chromatography (CHCl$_3$-EtOAc-MeOH mixture) to provide product, compound 15, 41 mg (82% yield) as a white foam. $^1$H NMR (CDCl$_3$) δ: 8.033 (2H, m), 7.81 (1H, m), 7.68 (1H, m), 7.57~7.33 (6H, m), 7.26~6.95 (5H, m), 6.42 (1H, s), 6.27 (1H, d, J=7.3 Hz), 4.66 (2H, m), 3.42 (2H, s), 3.37~3.31 (2H, m), 3.14~2.87 (5H, m), 2.55 (1H, dd, J=4.88, 15.13 Hz), 2.28 (3H, s), 1.83 (3H, s), 2.07~1.12 (12H, m), 1.42 (9H, s). FABMS ($^+$Ve), m/z 786 [MH$^+$], 769 [MH$^+$—NH$_3$].

Compound 16. A solution of compound 14 (51 mg, 0.058 mmol) in 3 ml of benzene containing phenethylamine (100 µl, 0.6 mmol 10 equivalents) was stirred at room temperature for 2.5 hr and benzene was evaporated. The residue was treated with TFA-water-triethylsilane (mixture (3.7 ml: 0.2 ml : 0.1 ml) for 1 hr and then taken by dryness under high vacuum at room temperature. 5 ml of water were added to the mixture, and the mixture was taken to dryness again to remove the remaining TFA. This procedure was repeated twice. The crude product obtained was dissolved in MeCH:H$_2$O (1:1, plus 0.1% TFA, 10 ml), filtered and purified by HPLC, using an Advantage C18 column (250 mm×20 mm dia.) with a flow rate: 10 ml/min and a linear gradient from 5% B in 100% B over 40 min.; solvent A: 0.1% aqueous TFA; solvent B: 0.1% TFA in MeCN. Compound 16 was obtained as a white solid (17.7 mg, 42.5%). $^1$H NMR (DMSO) δ: 9.33 (1H, s, —OH), 8.83 (1H, m), 8.46 (1H, d, J=7.81 Hz), 8.32 (1H, s), 8.09 (1H, m), 7.92 (2H, m), 7.74 (1H, m), 7.57~7.45 (6H, m), 7.28~7.13 (5H, m), 6.96 (2H, m), 6.69 (1H, s), 6.59 (1H, dd, J=7.82 Hz), 4.67 (1H, m), 4.40 (1H, m), 3.40 (2H, s), 3.31 (2H, q, J=6.35 Hz), 3.20~3.01 (5H, m), 2.87 (1H, dd, J=10.50, 15.20Hz), 2.76~2.68 (3H, m), 2.65~2.33 (1H, dd, J=6.34, 14.90 Hz), 1.96~1.18 (12H, m). FABMS ($^-$Ve), m/z 819.5 [M-H], 775.4 [M- H-CO$_2$]. HR-FABMS calcd for C$_{37}$H$_{43}$N$_5$O$_{10}$ m/z 716.2932 (M-H).

Compound 17. A solution of compound 15 (41 mg, 0.052 mmol) in 3 ml of benzene containing phenethylamine (100 µl 0.6 mmol, 10 equivalents) was stirred at room temperature for 2.5 hr, and at the end, the benzene was evaporated. The residue obtained was treated with TFA-water-triethylsilane mixture (3.7 ml : 0.2 ml : 0.1 ml) for 1 hr and then taken to dryness under high vacuum at room temperature. 4 ml of water were added and the mixture was taken to dryness again to remove the remained TFA. This procedure was repeated twice. The crude product obtained was dissolved in MeCH:H$_2$O (1:1, plus 0.1% TFA, 10 ml), filtered and purified by HPLC, using an Advantage C$_{18}$ column (250 mm×20 mm dia.) with a flow rate: 10 ml/min and a linear gradient from 5% B to 100% B over 40 min; solvent A: 0.1% aqueous TFA; solvent B: 0.1% TFA in MeCN. Product 106C-96 was obtained as a white solid (24.7.7 mg, 69%). $^1$H NMR (DMSO) δ:9.29 (1H, s, Br, —OH), 8.20 (2H, m), 8.08 (1H, m), 7.96 (1H, d, J=7.82 Hz), 7.90–7.87 (1H, m), 7.74 (1H, M), 7.53~7.33 (6H, m), 6.96 (1H, d, J=7.81 Hz), 6.90 (1H, s), 6.70 (1H, s), 6.64 (1H, d, J=7.81 Hz), 4.61 (1H, m), 4.36 (1H, m), 3.41 (2H, s), 3.17 (2H, m), 3.07~-2.93 (3H, m), 2.75~2.56 (3H, m), 1.78 (3H, s), 1.98~1.14 (12H, m), FABMS ($^+$Ve), m/z 710 [M+Na$^+$], 688 [NH$^+$], 671 (MH$^{30}$ —NH$_3$), HR-FABMS calcd for C$_{37}$H$_{46}$N$_5$O$_8$ (MH$^+$) m/z 688.3346.

Figure 3:
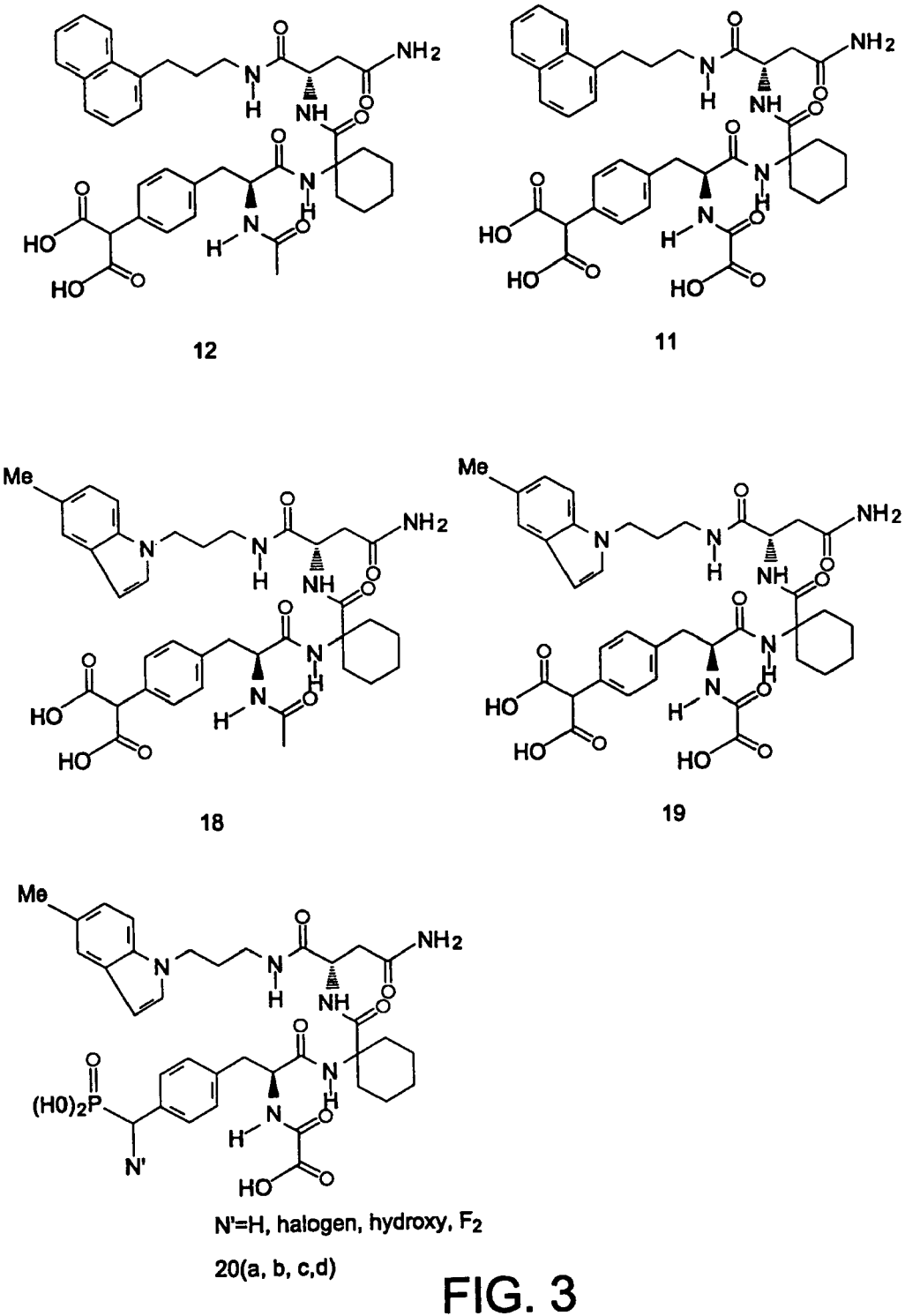
FIG. 3 depicts some other embodiments of the compounds of formula X in accordance with the present invention, particularly compounds 18–20.
Figure 4:
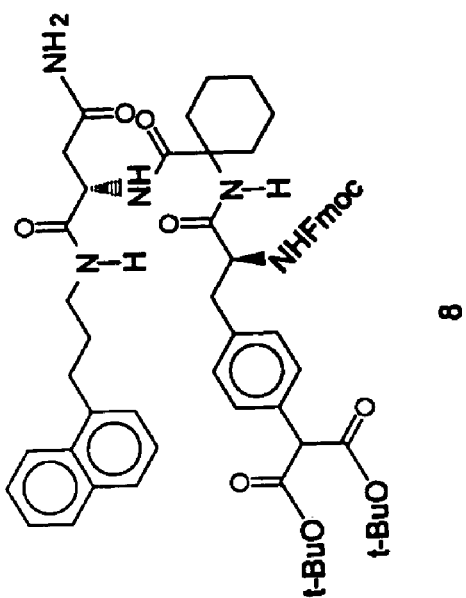
FIGS. 4–13 depict reaction schemes for preparing compounds 8–17, respectively.
Figure 4:
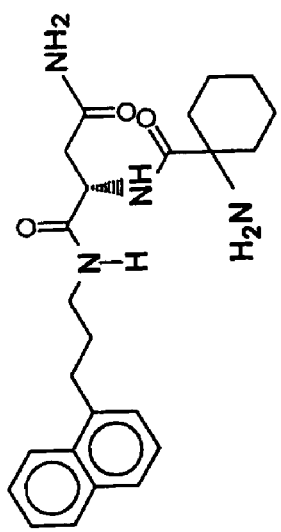
Figure 5:
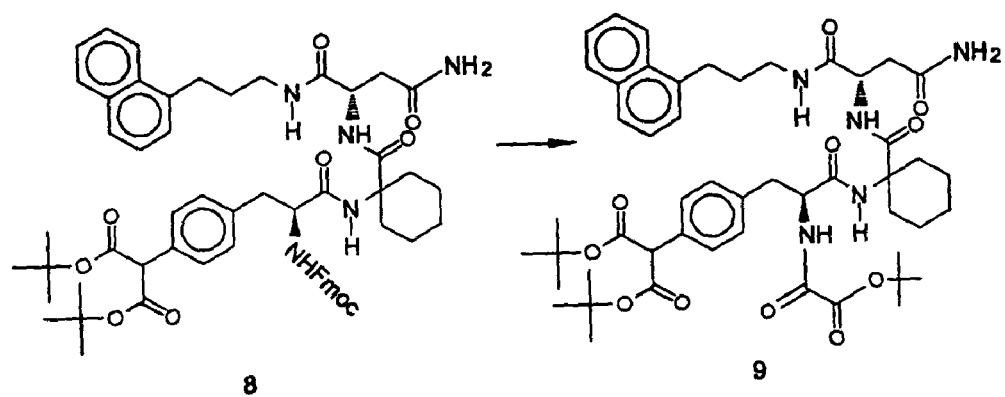
Figure 6:
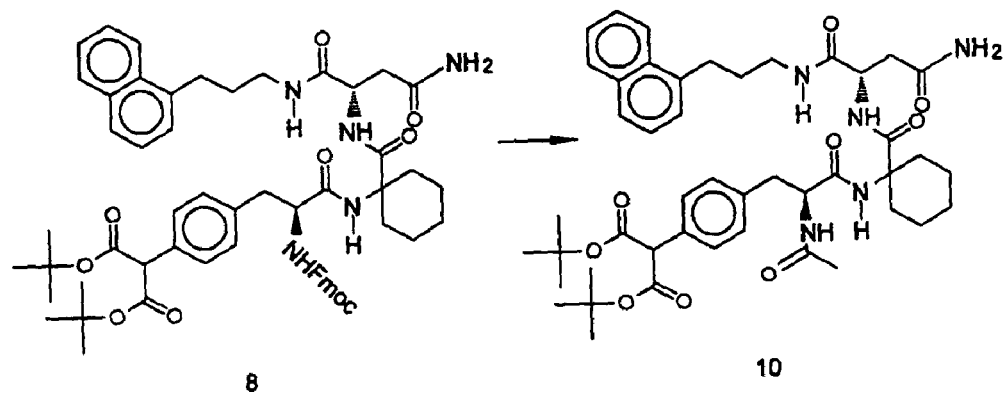
Figure 7:
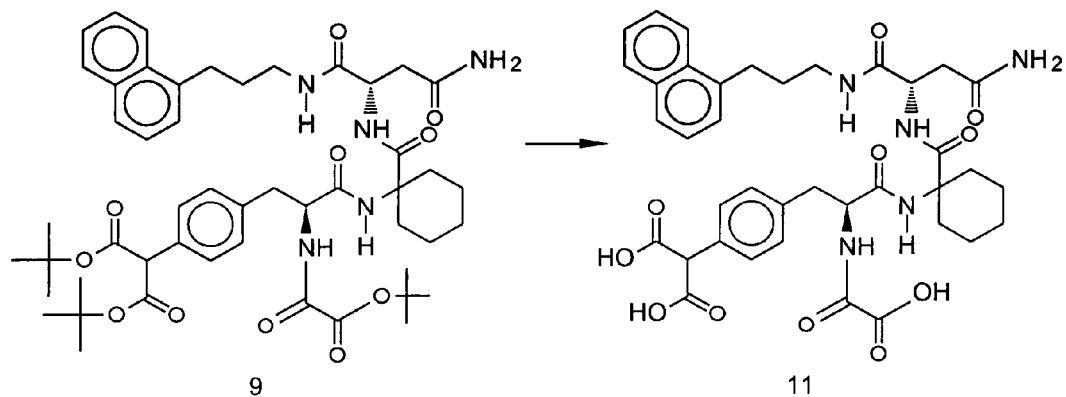
Figure 8:
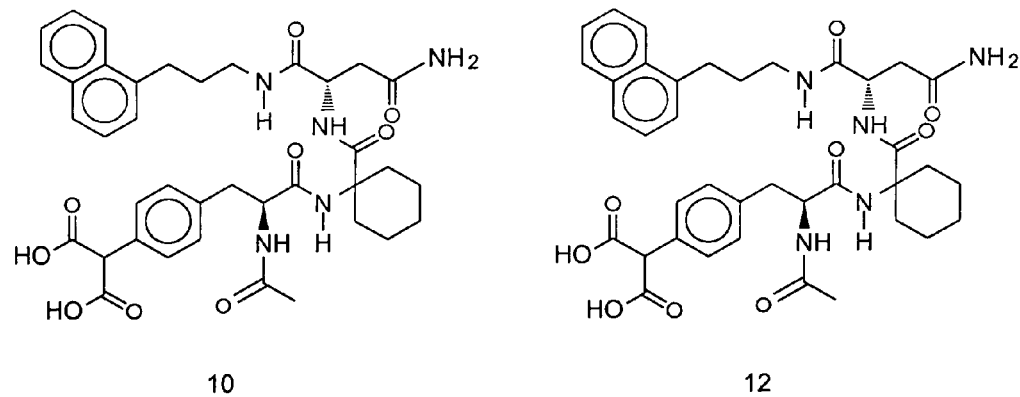
Figure 9:
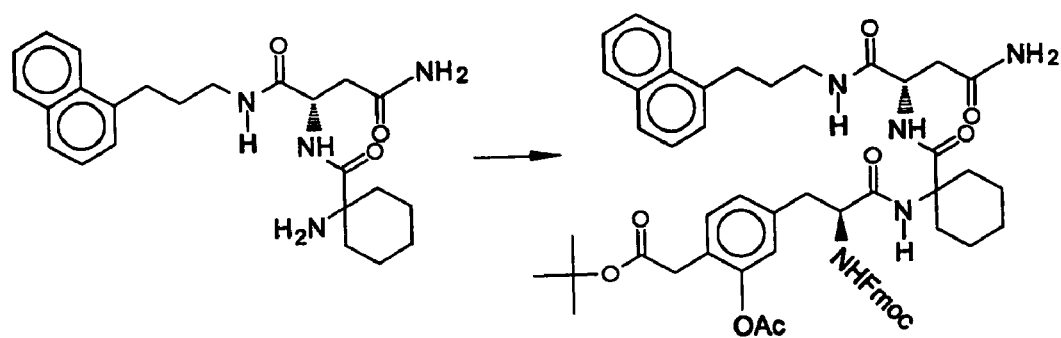
Figure 10:
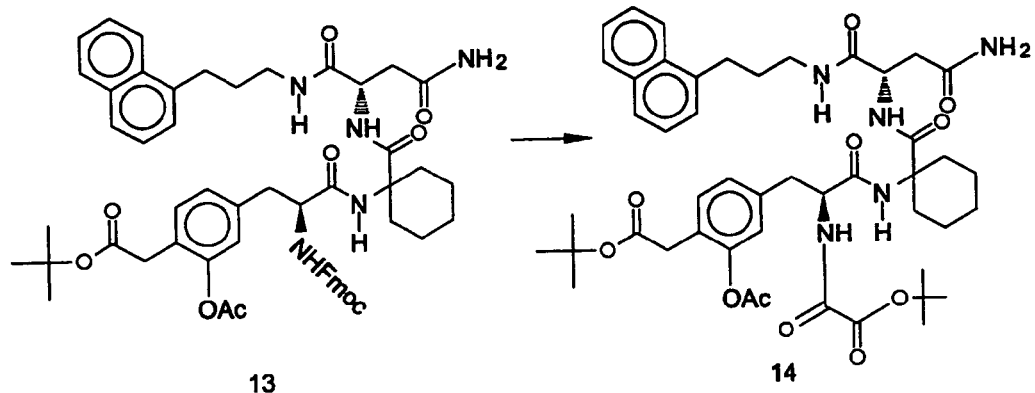
Figure 11:
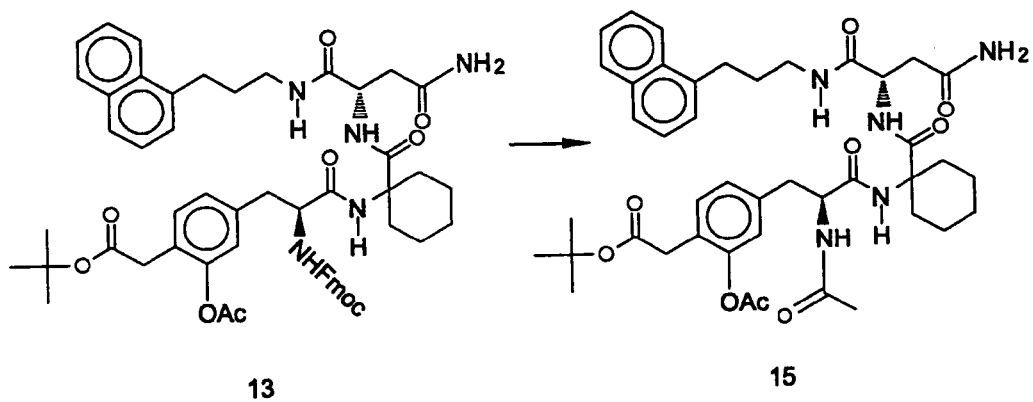
Figure 12:
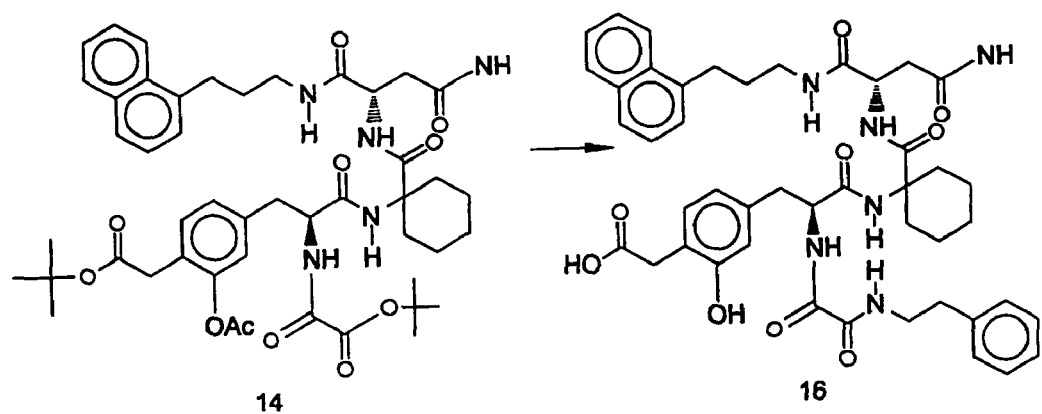
Figure 13:
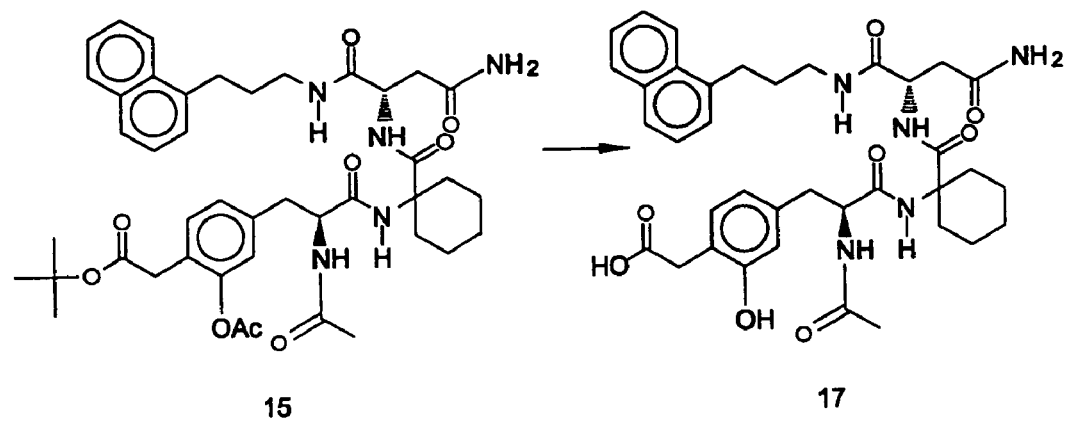

Additional examples of preparing compounds (18–20) of formula X are set forth in FIG. 3.

EXAMPLE 3

Figure 14:
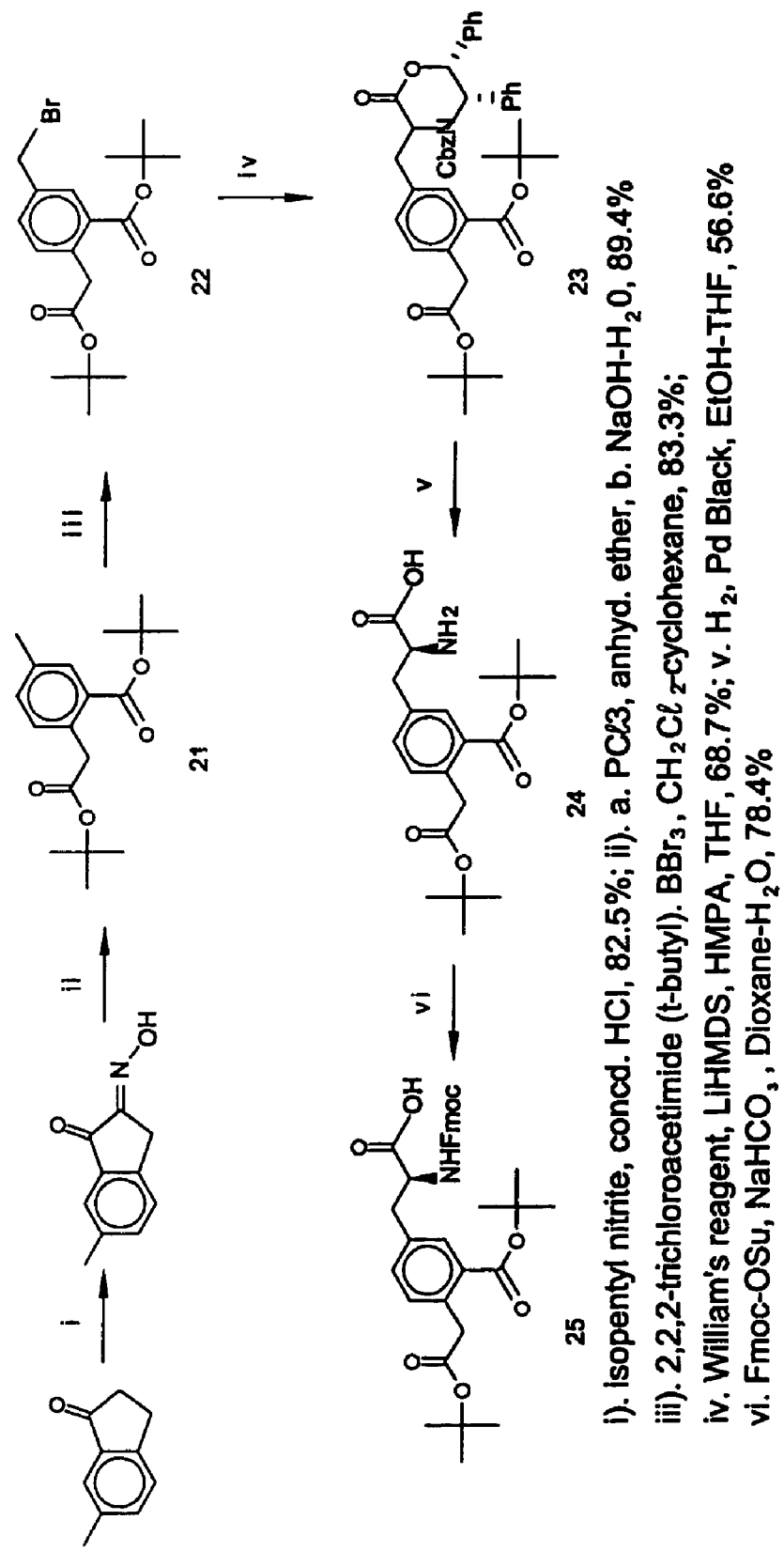
FIG. 14 depicts a reaction scheme for preparing compounds 21–25.

This Example illustrates a method of preparing some compounds of formula I. The reaction involved are schematically illustrated in FIG. 14.

2-Carboxymethyl-5-methyl-benzoic acid was prepared according to the published methods (*J. Org. Chem.*, 4689 (1962)).

2-Tert-butoxycarbonylmethyl-5-methyl benzoic acid tert-butyl ester (21). To a suspension of 2-carboxymethyl-5-methyl-benzoic acid (2.544 g, 13.1 mmol) in anhydrous dichloromethane (70 ml) held at 0° C. was added tert-butyl 2,2,2-trichloroacetimidate (11.47 mg, 52.4 mmol, 2 equivalents) in cyclohexane (85 ml). BBr$_3$ (0.52 ml) was then added, and the reaction mixture was raised to room temperature and stirred for 16 hr. Solid NaHCO$_3$ was added to quench the reaction, the solid precipitate was filtered off and washed with ether. The combined organic washing was evaporated to dryness, and the residue obtained was purified by silica gel chromatography to obtain 2-tert-butoxycarbonylmethyl-5-methyl benzoic acid tert-butyl ester 3.345 g (83.3%) as an oil. $^1$H NMR (CDCl$_3$): 7.718 (1H, s), 7.227 (1H, d, J=7.57 Hz), 3.910 (2H, s), 2.362 (3H, s), 1.584 (9H, s), 1.443 (9H, s). FABMS ($^+$Ve) m/z 307 [MH$^+$], 251 [MH$^+$—C$_4$H$_8$], 195 [MH$^{30}$ —2C$_4$H$_4$]. Anal. calcd. for C$_{18}$H$_{26}$O$_4$: C, 70.6; H, 8.6. Found: C, 70.82; H, 8.53.

2-Tert-butoxycarbonylmethyl-5-bromomethyl benzoic acid tert-butyl ester (22). 2- Tert-butoxycarbonylmethyl-5-methyl benzoic acid tert-butyl ester (4.751, 15.5 mmol) was dissolved in 75 ml of $CCl_4$. To the solution was added N-bromosuccinimide (2.90 g, 16.3 mmol, 1.05 equivalents) and benzoyl peroxide (180 mg). The reaction mixture was refluxed under an argon atmosphere overnight; the reaction mixture was then cooled to room temperature, and the solid precipitate was filtered off, and washed with hexanes, the combined organic was taken to dryness and the residue was purified by chromatography to obtain 2-tert-butoxycarbonylmethyl-5-bromomethyl benzoic acid tert-butyl ester 2.286 g (38.3% yield) as an oil. $^1$H NMR ($CDCl_3$): 7.920 (1H, d, J=2.2 Hz), 74.60 (1H, dd, J=1.95, 7.81 Hz), 7.193 (1H, d, J=7.81 Hz), 4.500 (2H, s), 3.953 (2H, s), 1.590 (9H, s), 1.444 (9H, s) FABMS ($^+$Ve), m/z 387 [$MH^+$, $^{81}Br$], 385 [$MH^+$, $^{79}Br$], 331 [$MH^+$—$C_4H_8$, $^{81}Br$], 329 [$MH^+$—$C_4H_8$, $^{79}Br$], 275 [$MH^+$—$2C_4H_8$, $^{81}Br$], 273 [$NH^+$—$2C_4H_8$, $^{79}Br$]. Anal. calcd. for $C_{18}H_{25}BrO_4$: C, 56.1; H, 6.5; Br, 20.7. Found: C, 56.27; H, 6.60; Br, 20.75.

Benzyl (3S,5S,6R)-3-{[3-tert-butoxycarbonyl-4-(tert-butoxycarbonylmethyl)phenyl]-methyl}-(−)-6-oxo-5,6-diphenyl-4-morpholine-carboxylate (23). To a solution of benzyl (2R,3S)-(−)-6-oxo-2,3-diphenyl-4-morpholine-carboxylate (2.298 g, 5.93 mmol) in anhydrous tetrahydrofuran (50 ml) and MPA (4.0 ml) cooled to −78° C. under an argon atmosphere was added lithium bis(trimethylsilyl)amide (1.0M solution in hexanes, 6.23 ml, 6.23 mmol, 1.05 equivalents). The reaction mixture was stirred at −78° C. for 1 hour. A solution of 2-tert-butoxycarbonylmethyl-5-bromomethyl benzoic acid tert-butyl ester (2.286 g, 5.93 mmol) in THF (10 ml) was added slowly at −78° C. via a syringe, and the mixture was stirred at −78° C. for 2 hours. The temperature was then raised to room temperature, and stirred overnight. The reaction mixture was quenched with aqueous $NH_4Cl$ (10 ml) and diluted with 35 ml of water. The mixture was extracted with ethyl acetate (50 ml×3), and the combined organics were washed successively with water, aqueous $NH_4Cl$, and brine, dried over $Na_2SO_4$. Concentration and purification by silica gel chromatography (hexanes-ethyl acetate, from 6:1 to 3:1) gave benzyl (3S,5S,6R)-3-{[3-tert-butoxycarbonyl-4-(tert-butoxycarbonylmethyl)phenyl]-methyl}-(−)-6-oxo-5,6-diphenyl-4-morpholine-carboxylate as a white foam. (2.8188 g, 68.7% yield). $^1$H NMR ($CDCl_3$) (two conformers were observed in a ratio of 2:5 at 23° C.) δ: 7.834 (1H, d, J=1.96 Hz), 7.417~7.317 (2H, m, overlapping), 7.230~7.046 (10 H, m, overlapping), 6.757~6.589 (4H, m, overlapping), 6.502 (1H, d, J=7.3 Hz, overlapping); major conformer; 5.352 (1H, dd, J=2.93, 6.59 Hz, —OOCCH—N), 5.113 (1H, J, J=12.2 Hz, $OCH_2Ph$), 4.931 (1H, d, J=12.20 Hz, $OCH_2Ph$), 4.881 (1H, d, J=2.93 Hz, COOCHPh—), 4.520 (1H, d, J=2.93 Hz, PhCHN—), 4.037 (1H, d, J=16.84 Hz, —$CH_2COOtBu$), 3.874 (1H, d, J=17.09 Hz, $NCH_2COOtBu$), 3.743 (1H, dd, J=6.84, 13.92 HZ), 3.440 (1H, dd, J=2.93, 13.91 HZ), 1.523 (9H, s), 1.452 (9H, s); miner conformer: 7.747 (1H, s), 5.708 (1H, d, J=2.20 Hz, —PhCHOOC—), 7.417~7.317 (2H, m, overlapping), 7.230~7.046 (10 H, m, overlapping), 6.757~6.589 (4H, m, overlapping), 6.502 (1H, d, J=7.3 Hz, overlapping), 5.248 (1H, dd, J=3.66. 7.72 Hz, —OOCCH-N), 5.287 (1H, d, J=11.97 Hz, $OCH_2Ph$), 5.117 (1H, d, J=12.5 Hz, $OCH_2Ph$), 5.047 (1H, d, J=2.93 Hz, COOCHPh—), 4.811 (1H, d, J,—17.09 Hz, —$CH_2COOtBu$), 3.512 (1H, dd, J=7.32, 13.91 Hz), 3.383 (1H, dd, J=3.42, 13.91 Hz), 1.557 (9H, s), 1.542 (9H, s); FABMS ($^-$Ve) m/z 690 [M-H], 634 [M-H-$C_4H_8$]. Anal. calcd. for $C_{42}H_{45}NO_8$; C, 72.9; H, 6.6; N, 2.0. Found: C, 73.07; H, 6.70; N, 1.95.

(3-tert-butoxycarbonyl-4-tert-butoxycarbonylmethyl)-L-phenylalamine (24). Benzyl (3S,5S,6R)-3-{[3-tert-butoxycarbonyl-4-(tert-butoxycarbonyl-methyl)phenyl]-methyl}-(−)-6-oxo-5,6-diphenyl-4-morpholine-carboxylate (2.7388 g, 3.96 mmol) was dissolved in THF-EtOH mixture (2:1, 24 ml) and hydrogenated over Pd black (250 mg) under high pressure (45 psi~20 psi or 310 kPa to about 138 kPa) at room temperature (24 hours). At the end, the palladium block was filtered off and washed with MeOH. The combined organic was concentrated to give a white sticky solid. This crude product was washed thoroughly with ether to remove 1,2-diphenylethane and dried under vacuum to obtain (3-tert-butoxycarbonyl-4-tert-butoxycarbonylmethyl)-L-phenylalanine as a white powder (851 mg, 56.6%). $^1$H NMR (DMSO) δ: 7.700 (1H, s), 7.376 (1H, d, J=76.6 Hz), 7.206 (1H, d, J=6.6 Hz), 3.876 (2H, s), 3.45~3.25 (2H, m), 3.154 (1H, dd, J=4.15, 14.16 Hz), 2.851 (1H, dd, J=7.56, 14.16 Hz), 1.514 (9H, s), 1.386 (9H, s) ppm; FABMS ($^+$Ve) m/z 380 [$MH^+$], 324 [$MH^+$—$C_4H_8$], 268 [$MH^+$—$2C_4H_8$]. Anal. calcd. for $C_{20}H_{29}NO_6$: C, 63.3; H, 7.7; N, 3.7. Found: C, 63.53; H, 7.72; N, 3.68.

N-Fmoc-(3-tert-butoxycarbonyl-4-tert-butoxycarbonylmethyl)-L-phenylalanine (25). A mixture of (3-tert-butoxycarbonyl-4-tert-butoxycarbonylmethyl)-L-phenylalanine (830 mg, 2.24 mmol), Fmoc-OSu (754 mg, 2.24 mmol) and $NaHCO_3$ (1.5 mg, 17.9 mmol, 8 equivalents) in 50 ml of dioxane-water (1:1) was stirred at room temperature overnight, and the reaction mixture was cooled to 0° C. and acidified with 180 ml of 0.2 M HCl. The reaction product was extracted with ethyl acetate (50 ml×3), the combined organics were washed with brine, dried ($Na_2SO_4$) and concentrated. The crude product was purified by silica gel flash chromatography ($CDCl_3$-EtOAc-MeOH) to provide N-Fmoc-(3-tert-butoxycarbonyl-4-tert-butoxycarbonylmethyl)-L-phenylalanine as a foam (1.032, 78.4%). $^1$H NMR (DMSO): 12.729 (1H, s, br), 7.874 (2H, d, J=7.57 Hz), 7.804 (1H, d, J=8.55 Hz), 7.754 (1H, s), 7.627 (2H, m), 7.450–7.194 (6H, m), 4.30–4.10 (4H, m), 3.861 (2H, s), 3.119 (1H, dd, J=4.39, 14.16 Hz), 2.910 (1H, dd, J=11.48, 13.18 Hz), 1.489 (9H, s), 1.372 (9H, s). FABMS ($^+$Ve), m/z 602 [$MH^+$], 490 [$MH^+$—2 $C_4H_8$]. HR-FABMS calcd for $C_{20}H_{29}NO_6$: 601.2676.

EXAMPLE 4

Figure 15:
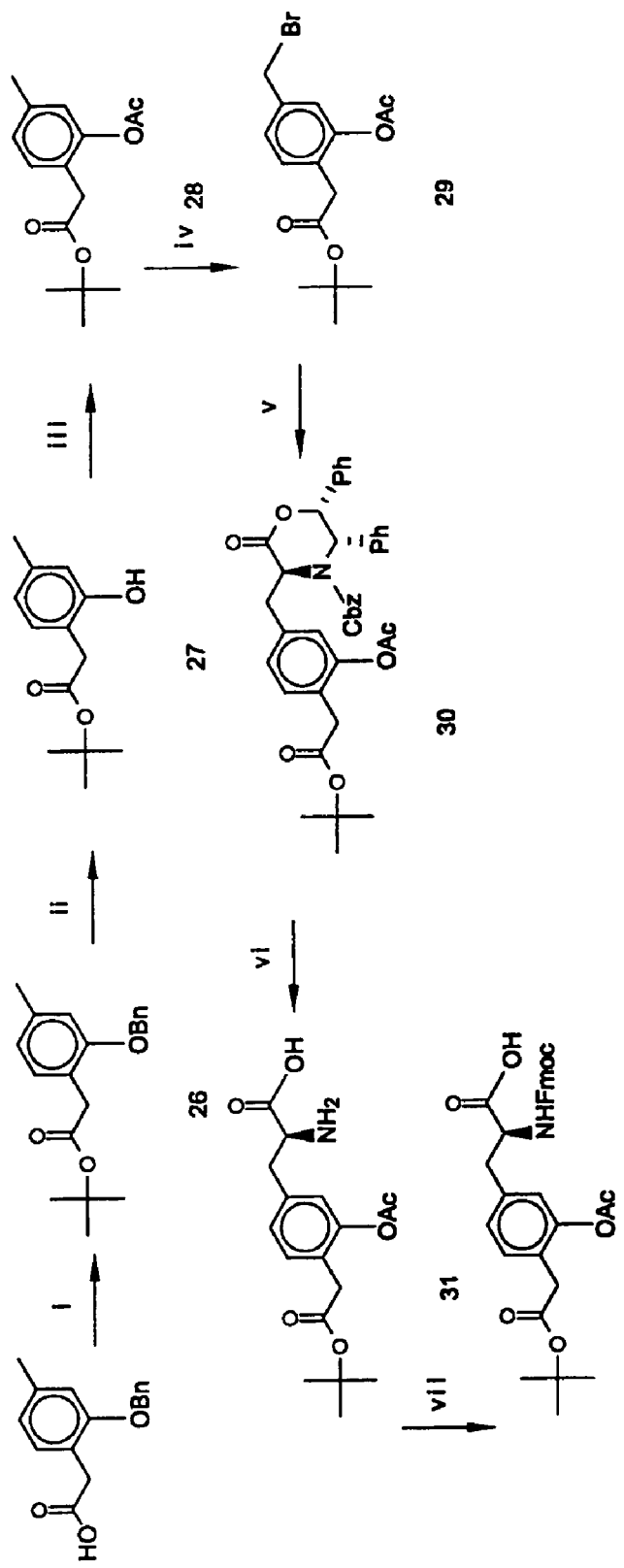
FIG. 15 depicts a reaction scheme for preparing compounds 26–32.

This Example illustrates a method of preparing some other embodiments of formula I. The reactions involved are schematically illustrated in FIG. 15.

[4-Methyl-2-(phenylmethoxy)phenyl]acetic acid was prepared according to the published methods (G. W. Rewcastle et al., J. Med. Chem., 32, 793–799 (1989)).

[4-Methyl-2-(phenylmethoxy)phenyl]acetic acid tert-butyl ester (26). To a solution of [4-methyl-2-(phenylmethoxy)phenyl]acetic acid (10.25 g, 40 mmol) in toluene (70 ml containing 2 drops of DMF) was added oxalyl chloride (4.0 ml, 46 mmol, 1.15 equivalents) dropwise, the mixture was stirred at room temperature for 5 hr then 44 ml of tert-butanol was added, the resulting solution was stirred at room temperature for 20 hr. The solvents were evaporated and the residue obtained was purified by chromatography on silica gel (EtOAc-hexanes, 1:40 to 1:25) to provide the desired product [4-methyl-2-(phenylmethoxy)-phenyl]acetic acid tert-butyl ester as an oil (11.70 g, 92.8% yield). $^1$H NMR ($CDCl_3$) δ: 7.521~7.364 (5H, m), 7.147 (1H, d, J=7.81 Hz), 6.810 (2H, m), 5.118 (2H, s), 3.629 (2H, S), 2.391 (3H, s), 1.461 (9H, s) ppm.

(2-Hydroxy-4-methylphenyl)acetic acid tert-butyl ester (27). To a solution of [4-methyl-2-(phenylmethoxy)phenyl]acetic acid tert-butyl ester (10.67 g, 34.2 mmol) in 125 ml of ethanol was added palladium block (200 mg), the mixture was hydrogenated (using a hydrogen balloon) at 30° C. for 10 hr. After the starting material disappeared completely (detected by TLC), the solid was filtered off, and the solvent was evaporated to give a crude product of (2-hydroxy-4-methylphenyl)acetic acid tert-butyl ester, 7.32 g, (96%) as white solid. $^1$H NMR (CDCl$_3$) δ: 7.931 (1H, s, br), 6.955 (1H, d, J=7.56 Hz), 6.799 (1H, s), 6.688 (1H, d, J=7.81 Hz), 3.551 (2H, S), 2.299 (3H, s), 1.472 (9H, s) ppm.

(2-Acetoxyl-4-methylphenyl)acetic acid tert-butyl ester (28). To a solution of (2-hydroxy-4-methylphenyl)acetic acid tert-butyl ester (4.45 g, 20 mmol) in pyridine (6.5 ml) was added acetyl anhydride (5.1 g, 50 mmol) at room temperature, and the resulting solution was stirred at room temperature overnight. The pyridine and the remaining acetyl anhydride were removed by applying high vacuum at 30° C. 20 ml of toluene were added to the residue, and the toluene was evaporated to remover the residual pyridine. The crude product obtained was purified by chromatography on silica gel to provide product (2-acetoxyl-4-methylphenyl)acetic acid tert-butyl ester (4.95 g, 94%) as an oil. $^1$H NMR (CDCl$_3$) δ: 7.175 (1H, d, J=7.81 Hz), 7.008 (1H, d, J=7.81 Hz), 6.904 (1H, s), 3.420 (2H, S), 2.341 (3H, s), 2.308 (3H, s), 1.430 (9H, s) ppm.

(2-Acetoxyl-4-bromomethylphenyl)acetic acid tert-butyl ester (29). To a solution of 2-(2-acetoxyl-4-methylphenyl)acetic acid tert-butyl ester (4.9 g, 18.5 mmol) in CCl$_4$ (50 ml) was added N-bromosuccinimide (3.29 g, 18.5 mmol, 1 equivalents) and benzoyl peroxide (100 mg), the reaction mixture was refluxed under argon for 3 hr. The reaction mixture was then cooled to room temperature. The solid precipitate was filtered off, and washed with hexanes, the combined organic was taken to dryness, and the residue obtained was purified by chromatography (Hexanes—EtOAc, 50:1 to 40:1) to give (2-acetoxy-4-bromomethylphenyl)acetic acid tert-butyl ester 2.467 g (38.8% yield) as an oil. $^1$H NMR (CDCl$_3$) δ: 7.290 (1H, d, J=7.81 Hz), 7.230 (1H, dd, J=1.71, 7.81 Hz), 7.158 (1H, d, J=1.71 Hz), 4.467 (2H, s), 3.462 (2H, S), 2.320 (3H s), 1.430 (9H, s) ppm. FABMS ($^+$Ve), m/z 345 [MH$^+$, $^{81}$Br], 343 [MH$^+$, $^{79}$Br], 389 [MH$^+$—C$_4$H$_8$, $^{81}$Br], 387 [MH$^+$—C$_4$H$_8$, $^{79}$Br]. Anal. calcd. for C$_{15}$H$_{19}$BrO$_4$; C, 52.5; H, 5.6; Br, 23.3. Found: C, 52.30; H, 550; Br, 23.44.

Benzyl (3S,5S,6R)-3-{[3-acetoxy-4-(tert-butoxycarbonylmethyl)phenyl]-methyl}-(−)-6-oxo-5,6-diphenyl-4-morpholine-carboxylate (30). To a solution of benzyl (2R,3S)-(−)-6-oxo-2,3-diphenyl-4-morpholine-carboxylate (2.47 g, 6.39 mmol) in anhydrous tetrahydrofuran (40 ml) and HMPA (4.4 ml) cooled to −78° C. under argon atmosphere was added lithium bis(trimethylsilyl)amide (1.0M solution in hexanes, 6.70 ml, 6.70 mmol, 1.05 equivalents). The reaction mixture was stirred at −78° C. for 1 hour. A solution of (2-acetoxyl-4-bromomethylphenyl)acetic acid tert-butyl ester (2.192 g, 6.39 mmol) in THF (10 ml) was added slowly at −78° C. via a syringe, and the reaction was allowed to proceed at −78° C. for 2 hours. The temperature was then raised to room temperature, and the mixture stirred overnight. The reaction mixture was quenched with aqueous NH$_4$Cl (10 ml) and diluted with 35 ml of water. The mixture was then extracted with ethyl acetate (50 ml×3), and the combined organics were washed successively with water, aqueous NH$_4$Cl, and brine, dried over Na$_2$SO$_4$. Concentration and purification by silica gel chromatography (hexanes-ethyl acetate, from 6:1 to 3:1) gave benzyl (3S,5S,6R)-3-{[3-acetoxyl-4-(tert-butoxycarbonylmethyl)phenyl]-methyl}-(−)-6-oxo-5,6-diphenyl-4-morpholine-carboxylate as a white foam (2.070 g, 50.0% yield). $^1$H NMR (CDCl$_3$) (two conformers were observed in a ratio of 2.7:1 at 23° C.) δ: 7.396 (1H, m, overlapping), 7.279~6.959 (12H, m, overlapping), 6.869~6.696 (3H, m, overlapping; major conformer: 6.50 (2H, d, J=7.32 Hz), 5.317 (1H, dd, J=2.68, 6.10 Hz, —CHNCOO), 5.030 (2H, s, OCH$_2$Ph), 4.999 (1H, d, J=2.93 Hz, —PhCHOOC—), 4.315 (1H, d, J=3.18 Hz, —PhCHN—), 3.777 (1H, dd, J=5.86, 13.67 Hz, —CH$_2$—CHNCOO), 3.547~3.30 (3H, m, overlapping, tBuOOCCH$_2$—, —CH$_2$—CHNCOO), 2.313 (3H, s), 1.411 (9H, s) ppm; minor conformer: 6.586 (2H, d, J=7.08 Hz), 5.25 (1H, m, —CHNCOO), 5.134 (2H, s, OCH$_2$Ph), 5.063 (1H, d, J=2.93 Hz, —PhCHOOC—), 4.484 (1H, d, J=2.69 Hz, PhCH—), 3.597~3.30 (4H, m, overlapping, tBuOOCCH$_2$—, —CH$_2$—CHNCOO), 2.329 (3H, s), 1.590 (9H, s) ppm; FABMS ($^+$Ve) m/z 594 [MH$^+$—C$_4$H$_8$], 550 [MH$^+$—CO$_2$]. Anal. calcd. for C$_{42}$H$_{45}$NO$_8$: C, 72.1; H, 6.1; N, 2.2. Found: C, 72.10; H, 6.15; N, 2.13.

[3-Acetoxyl-4-(tert-butoxycarbonyl)methyl]-L-phenylalanino (31). Benzyl (3S,5S,6R)-3-{[3-acetoxyl-4-(tert-butoxycarbonylmethyl)phenyl]-methyl}-(−)-6-oxo-5,6-diphenyl-4-morpholine-carboxylate (1.50 g, 2.16 mmol) was dissolved in THF-EtOH mixture (1:2, 18 ml) and hydrogenated over Pd black (200 mg) under high pressure (50 psi~20 ps or 345 kPa to about 138 kPa i) at room temperature till all the starting material was transformed to the desired product. The mixture was filtered off and the solid obtained was washed with MeOH. The combined organics was concentrated to give a white sticky solid. The solid was washed thoroughly with ether to remove 1,2-diphenylethane and dried under vacuum to 3-acetoxyl-4-(tert-butoxycarbonyl)methyl]-L-phenylalanine as a white powder (857 mg, 100%). $^1$H NMR (DMSO) δ: 8.35 (1H, s, br), 7.274 (1H, d, J=7.57 Hz), 7.122 (1H, d, J=7.57 Hz), 7.049 (1H, s), 4.155 (1H, m), 3.448 (2H, s), 3.320 (2H, m), 3.093 (2H, d, J=6.10 Hz), 2.263 (3H, s), 1.385 (9H, s) ppm; FABMS ($^-$Ve) m/z 336 [M-H]. Anal. calcd. for C$_{17}$H$_{23}$NO$_6$: C, 60.5; H, 6.9; N, 4.2. Found: C, 59.09; H, 6.83; N, 3.32.

N-Fmoc-[3-acetoxyl-4-(tert-butoxycarbonyl)methyl]-L-phenylalanine (32). A mixture of [3-acetoxyl-4-(tert-butoxycarbonyl-methyl]-L-phenylalanine (857 mg, 2.16 mmol), Fmoc-OSu (727 mg, 2.16 mmol) and NaHCO$_3$ (906 mg, 10.8 mmol, 5 equivalents.) In 48 ml of dioxane-water (1:1) was stirred at room temperature overnight; the reaction mixture was then cooled to 0° C. and acidified with 180 ml of 0.2 M HCl. The product was extracted with ethyl acetate (30 ml×3), and the combined organic extract was washed with brine, dried (Na$_2$SO$_4$), and concentrated. The crude product obtained was purified by silica gel chromatography (CDCl$_3$-EtOAc-MeOH) to provide N-Fmoc-[3-acetoxyl-4-(tert-butoxycarbonyl)methyl]-L-phenylalanine as a white solid (510 mg, 39.5%). $^1$H NMR (DMSO) δ: 12.70 (1H, s, br), 7.884 (2H, d, J=7.33 Hz), 7.773 (2H, m), 7.433~7.043 (8H, m), 4.365~4.102 (4H, m), 3.405 (2H, s), 3.200 (2H, m), 2.925~2.80 9(1H, m), 2.206 (3H, s), 1.356 (9H, s) ppm. FABMS ($^-$Ve) m/z 711.6 [M-H=NBA], 558.5 (M-H). HR-FABMS calcd for C$_{32}$H$_{32}$NO$_6$ [M-H] m/z 558.2128.

EXAMPLE 5

Figure 16:
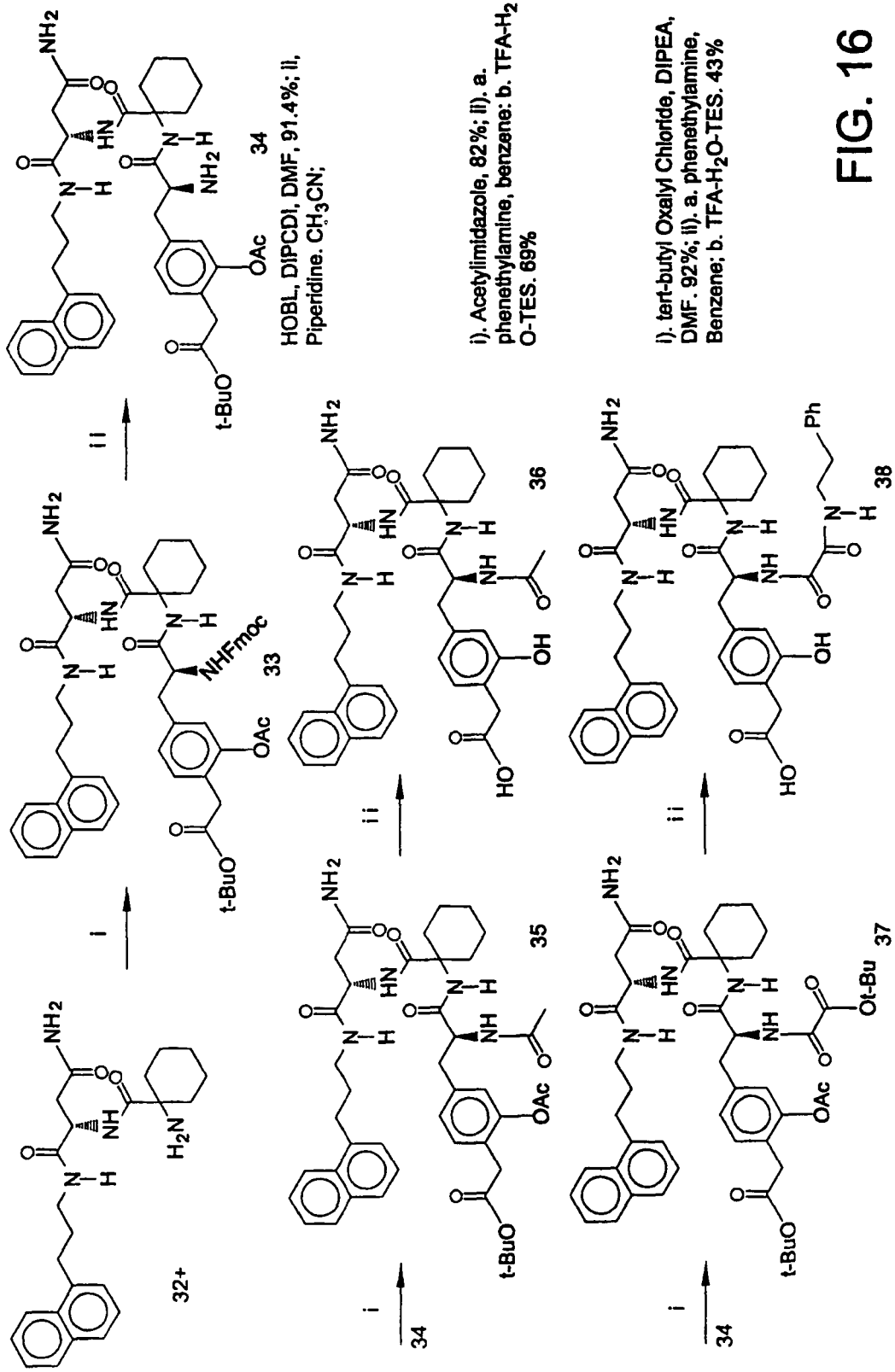
FIG. 16 depicts a reaction scheme for preparing compounds 33–38.
Figure 18:
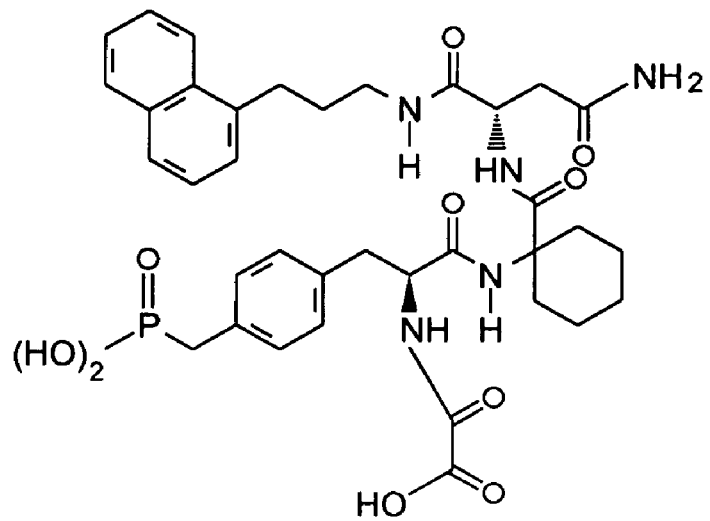
FIG. 18 depicts the formulas of compounds #126 and A referred to in FIG. 17.
Figure 18:
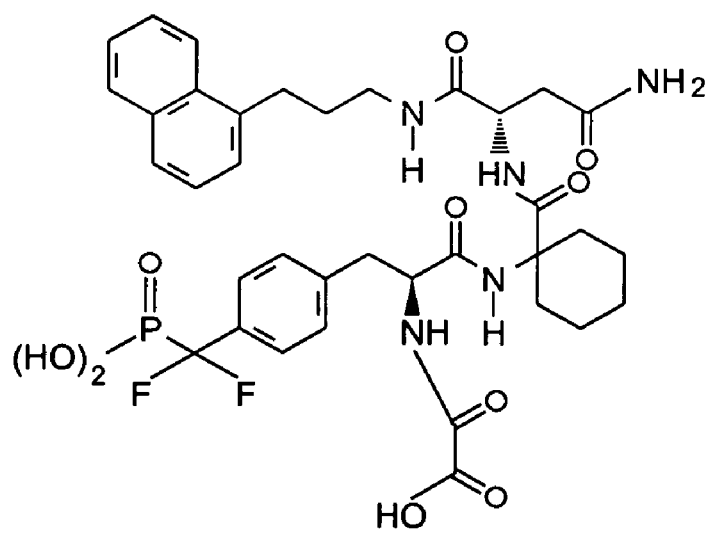

This Example illustrates a method of preparing additional embodiments of formula X. The reactions involved are schematically illustrated in FIG. 16.

EXAMPLE 6

This Example illustrates the biological activity of the compounds of formula X as Grb2 SH2 domain binding inhibitors.

Cell lines wee obtained from the American Type Culture Collection (Rockville, Md.) and Lombardi Cancer Center, Georgetown University Medical Center. Cells were routinely maintained in improved minimal essential medium (IMEM, Biofluids, Rockville, Md.) with 10% fetal bovine serum. Cultures were maintained in a humidified incubator at 37° C. and 5% $CO_2$.

The Biacore Binding Assay

Inhibition of SH2 domain binding was determined by the Surface Plasmon Resonance (SPR) method. The solution $IC_{50}$ values for peptide binding inhibition were measured as described in Yao et al., *J. Med. Chem.*, 42, 25–35 (1999). Compounds 11, 12 and 20a had $IC_{50}$ average values of 155 nM, 500 nM, and 117 nM, respectively.

Assay of Cell Growth and Proliferation Inhibition by GrB2 inhibitors

The effect of Grb2 inhibitors on protein synthesis was determined by two growth assays. The first assay, inhibition of cell proliferation assays were carried out an on plastics to directly measure the cell killing activity. The results obtained are set forth in FIG. 17. Cells that have amplified erbB-2 signaling such as the MDA-453 cells are inhibited by treatment with the tested inhibitors. Cells that do not utilized the activation of Grb2 or have down-stream activation of Grb2 such as MDA-231 (containing mutant ras protein) are not inhibited by treatment with the tested Grb2 inhibitors.

The second assay, a soluble tetrazolium/formazan (XTT) assay for cell growth in a 96-well plate was performed. Cells (2,000–4,000 cells/well) were grown in IMEM medium with 10% FBS and were treated with increasing concentrations of Grb2 inhibitors (1–50 uM). After 6–8 days culture, XTT (1.0 mg/ml plus PMS at 1.53 mg/ml) was added to each well and incubated for four hours at 37° C. Absorbance at 450 nm was measured with the Dynatech Model MR700. The results obtained showed that the compounds of the present invention have cell killing activity.

Inhibition of MAP Kinase

MAP kinases function in a protein kinase cascade that plays a critical role in the regulation of cell growth and differentiation. MAP kinases are activated by a wide variety of signals including growth factors, cytokines and hormones through Grb2 and other signaling proteins. The inhibition of MAP kinase in MDA-453 cells treated with growth factor heregulin (HRG) by MAP kinase specific antibody was measured. $1–2\times10^6$ cells were plated into 100 mm dishes with 10% FBS. Cells were washed twice with ice-cold PBS and lysed in 1 ml of lysis buffer (50 mM Tris-HCL, pH 7.4, 150 mM NaCl, 5 mM $MgCl_2$, 1% Triton X-100, 5 mM EDTA, 5 mM EGTA, 1 mM PMSF, 50 μg/ml approtinin, 50 μg/ml leupeptin, and 2 mM sodium orthovanadate). The protein concentration was determined by BCA method (Pierce, Rockford, Ill.). 50 μg of protein was subjected to 8–20% SDS-PAGE gel (Novex, San Diego, Calif.) and transferred to a nitrocellulose membrane. Activation of MAP kinase was detected with a specific antibody, i.e., phospho-p44/42 MAP kinase antibody (New England BioLabs) and visualized with ECL (Amersham, Arlington Heights, Ill.). The blotting results obtained confirmed that over 60% inhibition was achieved with compound 11.

Figure 19:
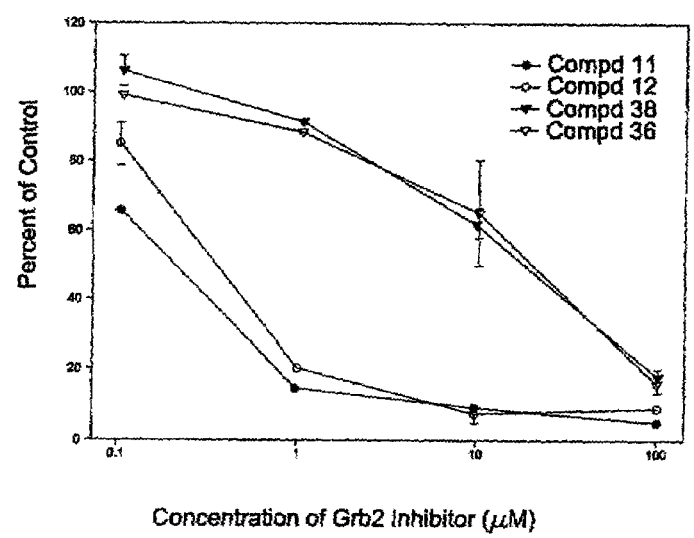
FIG. 19 depicts the results of an ELISA assay and shows that the compounds of the present invention have Grb2 inhibitory effect.

The Grb2 binding inhibition also was determined by carrying out an ELISA assay. The results obtained are set forth in FIG. 19. Compounds 11 and 12 were effective in inhibiting Grb2 binding.

In a separate set of experiments, the Biacore Binding Assays was compared to an ELISA assay, and excellent agreement was observed between the two assays.

EXAMPLE 7

This Example illustrates an advantage of the compounds of the present invention. When used in conjunction with chemotherapeutic drugs, synergistic effects have been observed.

Compound 126 inhibited colony formation of HBC BT-474 and MDA-453 cell lines. The soft agar colony formation was tested as follows. Cells in suspension (10,000 cells/ml) were mixed with 0.33% agarone and plated on top of a layer with 1% agarose. The next day, different concentrations of the inhibitor mixed with 1 ml of the culture medium were added to the top layer and incubated for two weeks. The number of colonies greater than 80 μm formed were counted on a Bausch and Lomb Image analysis system. In the combination therapy, chemotherapeutic drugs were mixed with 1 ml of the culture medium and were added to the top layer and incubated for two weeks.

Figure 20:
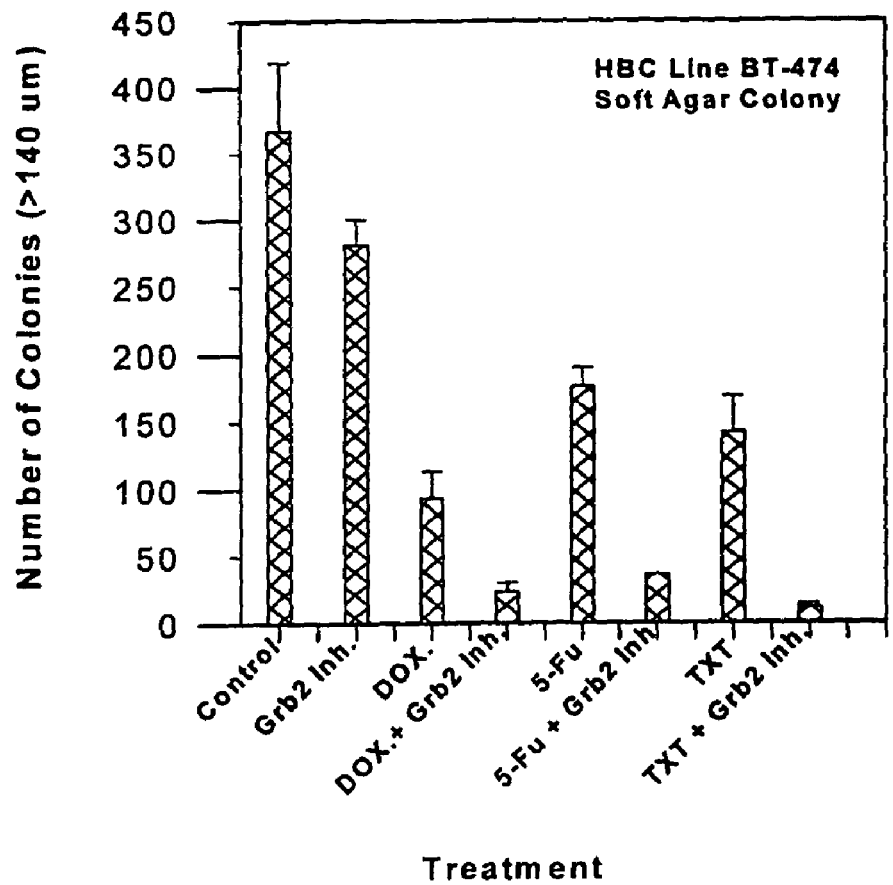
FIG. 20 depicts the synergistic effect of a combination treatment of a Grb2 inhibitor (compound #126) with certain chemotherapy drugs.

FIG. 20 depicts the synergistic effect observed when compound 126 was used in conjunction with the chemotherapeutic drugs on the HBC BT-474 cell line. Treatment with paclitaxel ("TXT" in the Figure), doxorubicin ("DOX"), and 5-fluorouracil ("5-Fu") in combination with the inhibitor resulted in a greater inhibition of Her-2/neu-overexpressing cancer cells than that was observed with the chemotherapeutic drug alone.

The references cited herein are hereby incorporated by reference in their entireties. While this invention has been described with an emphasis upon several embodiments, it will be obvious to those of ordinary skill in the art that variations of the embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of the formula:

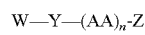

wherein n is 1 to 15;
  Y is a phenylalanyl radical having a phenyl ring, an amine end, a carboxyl end, and a —$CH_2$CH< group attached to the phenyl ring at the —$CH_2$ and the amine end and the carboxyl end attached to the CH<, the phenyl ring having one or more substituents selected from the group consisting of hydroxyl, carboxyl, formyl, carboxylalkyl, carboxyalkyloxy, dicarboxylalkyl, dicarboxyalkyloxy, dicarboxyhaloalkyl, dicarboxyhaloalkyloxy, and phosphonoalkyl, phosphonohaloalkyl, wherein the alkyl portion of the substituents of the phenyl ring may be unsubstituted or substituted with a substituent selected from the group consisting of halo, hydroxy, carboxyl, amino, aminoalkyl, alkyl, and alkoxy;
  W is a moiety attached to the nitrogen of Y and is selected from the group consisting of alkylcarbonyl, oxalyl, alkylaminooxalyl, arylaminooxalyl, arylalkylaminooxalyl, alkoxyoxalyl, carboxyalkyl carbonyl, heterocyclyl carbonyl, heterocyclylalkyl carbonyl, arylalkyl heterocyclylalkyl carbonyl, aryloxycarbonyl, and arylalkoxycarbonyl, wherein the aryl and alkyl portions of W may be unsubstituted or substituted with a substituent selected from the group consisting of halo, hydroxy, aminoalkyl, alkyl, and alkoxy; and the heterocyclyl portion of W contains at least 4 hereto atoms selected from the group consisting of O, N, and S;

AA is an amino acid, the amine end of which is attached to the carboxyl end of Y; and Z is arylalkylamino or aryl heterocyclyl $C_1$–$C_6$ alkylamino wherein an aryl group, which may be substituted or unsubstituted, is linked to a heterocyclyl group; wherein aryl is a carbocyclic aryl;

or a salt thereof;

with the proviso that Z is not arylalkylamino when W is oxalyl or acetyl and the phenyl ring of phenylalanyl contains a hydroxyl, malonyl difluoromethyl, malonyloxy, carboxyalkyloxy, phosphonodifluoromethyl, or phosphonomethyl substituted on the phenyl, ring at a position para to the —CH$_2$CH< group and the ortho and meta positions are unsubstituted and the proviso that Z is not arylalkylamino when W is arylalkoxycarbonyl and the substituent on the phenyl ring of Y is phosphonomethyl.

2. A compound of the formula W—Y—(AA)$_n$-Z wherein n is 1 to 15;

Y is a phenylalanyl radical having a phenyl ring, an amine end, a carboxyl end, and a —CH$_2$CH< group attached to the phenyl ring at the —CH$_2$ and the amine end and the carboxyl end attached to the CH<, the phenyl ring having one or more substituents selected from the group consisting of hydroxyl, carboxyl, formyl, carboxy $C_1$–$C_6$ alkyl, carboxy $C_1$–$C_6$ alkyloxy, dicarboxy $C_1$–$C_6$ alkyl, dicarboxy $C_1$–$C_6$ alkyloxy, dicarboxyhalo $C_1$–$C_6$ alkyl, dicarboxyhalo $C_1$–$C_6$ alkyloxy, and phosphono $C_1$–$C_6$ alkyl, phosphonohalo $C_1$–$C_6$ alkyl, wherein the alkyl portion of the substituents of the phenyl ring may be unsubstituted or substituted with a substituent selected from the group consisting of halo, hydroxy, carboxyl, amino, aminoalkyl, $C_1$–$C_6$ alkyl, and $C_1$–$C_6$ alkoxy;

W is a moiety attached to the nitrogen of Y and is selected from the group consisting of $C_1$–$C_6$ alkylcarbonyl, oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl, aryl $C_1$–$C_6$ alkyl heterocyclyl $C_1$–$C_6$ alkyl carbonyl, aryloxycarbonyl, and aryl $C_1$–$C_6$ alkoxycarbonyl, wherein the aryl and alkyl portions of W may be unsubstituted or substituted or substituted with a substituted selected from the group consisting of halo, hydroxy, amino $C_1$–$C_6$ alkyl, $C_1$–$C_6$ alkyl, and $C_1$–$C_6$ alkoxy; and the heterocyclyl portion of W contains at least 4 hetero atoms selected from the group consisting of O, N and S;

AA is an amino acid, the amine end of which is attached to the carboxyl end of Y; and Z is aryl $C_1$–$C_6$ alkylamino or arylheterocyclyl $C_1$–$C_6$ alkylamino wherein an aryl group is linked to a heterocyclyl group; wherein aryl is a carbocyclic aryl group;

or a salt thereof;

with the proviso that Z is not aryl $C_1$–$C_6$ alkylamino when W is oxalyl or acetyl and the phenyl ring of phenylalanyl contains a hydroxyl, dicarboxyhaloalkyl, dicarboxylalkoxy, carboxyalkyloxy, phosphonoalkyl, or phosphonohaloalkyl substituent of the phenyl ring at a position para to the —CH$_2$CH< group and the ortho and meta positions are unsubstituted and the proviso that Z is not arylalkylamino when W is acyl methoxycarbonyl when the substituent on the phenyl ring of Y is phosphonomethyl.

3. A compound of the formula:

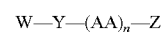

W—Y—(AA)$_n$—Z wherein n is 1 to 15;

W is a moiety attached to the nitrogen of Y and is selected from the group consisting of $C_1$–$C_6$ alkylcarbonyl, oxalyl, $C_1$–$C_6$ alkylaminooxalyl, arylaminooxalyl, aryl $C_3$–$C_6$ alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl, aryl $C_1$–$C_6$ alkyl heterocyclyl $C_1$–$C_6$ alkyl carbonyl, aryloxycarbonyl, and aryl $C_1$–$C_6$ alkoxycarbonyl, wherein the aryl and alkyl portions of W may be unsubstituted or substituted with a substituent selected from the group consisting of halo, hydroxy, carbonyl, amino, amino $C_1$–$C_6$ alkyl, $C_1$–$C_6$ alkyl, and $C_1$–$C_6$ alkoxy; and the heterocyclyl portion of W contains at least 4 hetero atoms selected from the group consisting of O, N, and S;

AA is an amino acid, the amine end of which is attached to the carboxyl end of Y; and Z is aryl $C_1$–$C_6$ alkylamino or arylheterocyclyl $C_1$–$C_6$ alkylamino wherein an aryl group is linked to a heterocyclyl group; wherein aryl is a carobcyclic aryl group;

or a salt thereof;

wherein Y is of the formula XI:

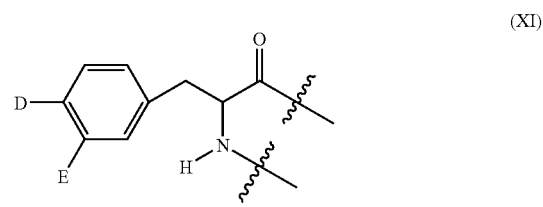

(XI)

wherein D has the formula XII, XIII, or XIV;

(XII)

(XIII)

-continued

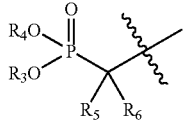
(XIV)

wherein $R_3$ and $R_4$ may be the same or different and are selected from the group consisting of hydrogen, $C_1$–$C_6$ alkyl, aryl, aryl $C_1$–$C_6$ alkyl, $C_1$–$C_6$ alkaryl, and heteroaryl; and $R_5$ and $R_6$ may be the same or different and are selected from the group consisting of hydrogen, halo, hydroxy, amino, and $C_1$–$C_6$ alkoxy; and E is selected from the group consisting of hydrogen, $C_1$–$C_6$ alkyl, $C_1$–$C_6$ alkylcarbonyl, carboxyl, and $C_1$–$C_6$ alkylcarbonyl $C_1$–$C_6$ alkyl;

with the proviso that Z is not aryl $C_1$–$C_6$ alkylamino when W is oxalyl or acetyl and D is hydroxyl, dicarboxyhaloalkyl, dicarboxyalkoxy, carboxyalkyloxy, alkoxycarbonylalkyl, phosphonoalkyl, or phosphonohaloalkyl and E is hydrogen.

4. The compound of claim 3, wherein D is of formula XII.

5. The compound of claim 3, wherein D is of formula XIII.

6. The compound of claim 3, wherein D is of formula XIV.

7. The compound of claim 4, wherein E is hydrogen.

8. The compound of claim 4, wherein E is carboxyl.

9. The compound of claim 4, wherein $R_3$, $R_5$, and $R_6$ are hydrogen.

10. The compound of claim 6, wherein $R_3$ and $R_4$ are hydrogen.

11. The compound of claim 1, wherein W is selected from the group consisting of $C_1$–$C_6$ alkylcarbonyl, oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl, aryl $C_1$–$C_6$ alkyl heterocyclyl $C_1$–$C_6$ alkyl carbonyl, aryloxycarbonyl, and aryl $C_1$–$C_6$ alkoxycarbonyl, wherein the aryl and alkyl portions of W may be unsubstituted or substituted with a substituent selected from the group consisting of halo, hydroxy, carboxyl, amino, amino $C_1$–$C_6$ alkyl, $C_1$–$C_6$ alkyl, and $C_1$–$C_6$ alkoxy; and the heterocyclyl portion of W contains at least 4 hereto atoms selected from the group consisting of O, N, and S.

12. The compound of claim 1, wherein Z is aryl $C_1$–$C_6$ alkylamino.

13. The compound of claim 12, wherein the aryl portion of Z has the formula:

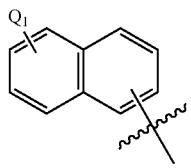

wherein $Q_1$ is hydrogen or a substituent selected from the group consisting of hydroxyl, halo, $C_1$–$C_6$ alkyl, $C_1$–$C_6$ alkoxy, amino, and $C_1$–$C_6$ acylamino.

14. The compound of claim 1, wherein the aryl heterocyclyl portion of Z has the formula:

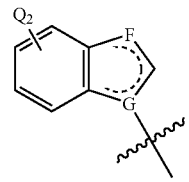

wherein $Q_2$ is hydrogen or a substituent selected from the group consisting of hydroxyl, halo, $C_1$–$C_6$ alkyl, $C_1$–$C_6$ alkoxy, amino, and $C_1$–$C_6$ acylamino, and F and G are independently selected from the group consisting of C, N, O, and S; with the proviso that F and G are not simultaneously C.

15. The compound of claim 1, wherein said amino acid is selected from the group consisting of glycine, alanine, valine, norvaline, leucine, iso-leucine, norleucine, α-amino n-decanoic acid, serine, homoserine, threonine, methionine, cysteine, S-acetylaminomethyl-cysteine, proline, trans-3- and trans-4-hydroxyproline, phenylalanine, tyrosine, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, tryptophan, indoline-2-carboxylic acid, 1,2,3,4-tetrahydroisoquinonline-3-carboxylic acid, aspartic acid, asparagine, aminomalonic acid, aminomalonic acid monoamide, glutamic acid, glutamine, histidine, arginine, lysine, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

16. A pharmaceutical composition comprising a pharmaceutically acceptable carrier and a compound of claim 1.

17. A compound of the formula:

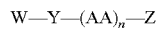

wherein n is 0 to 15;
Y is a phenylalanyl radical having a phenyl ring, an amine end, and a carboxyl end, a —CH$_2$CH< group, attached to the phenyl ring at the CH$_2$ and the amine end and the carboxyl end are attached to the CH<, the phenyl ring having the following substituent or a combination of substituents: (i) dicarboxy $C_1$–$C_6$ alkyl, (ii) hydroxyl and carboxy $C_1$–$C_6$ alkyl, (iii) carboxyl and carboxy $C_1$–$C_6$ alkyl, or (iv) dicarboxyhalo $C_1$–$C_6$ alkyloxy; or an ester of (i), (ii), (iii), or (iv); wherein the alkyl portion of the substituents of the phenyl ring may be unsubstituted or substituted with a substituted with a substituent selected from the group consisting of, hydroxy, carboxyl, amino, aminoalkyl, $C_1$–$C_6$ alkyl, and $C_1$–$C_6$ alkoxy;
W is a moiety attached to the nitrogen of Y and is selected from the group consisting of $C_1$–$C_6$ alkylcarbonyl, oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl, aryl $C_1$–$C_6$ alkyl heterocyclyl $C_1$–$C_6$ alkyl carbonyl, aryloxycarbonyl, and aryl $C_1$–$C_6$ alkoxycarbonyl, wherein the aryl and alkyl portions of the W may be unsubstituted or substituted with a substituent selected from the group consisting of halo, hydroxy, carboxyl, amino, amino $C_1$–$C_6$ alkyl, $C_1$–$C_6$ alkyl, and $C_1$–$C_6$ alkoxy; and the heterocyclyl portion of W contains at least 4 hetero atoms selected from the group consisting of O, N, and S;

AA is an amino acid, the amine end of which is attached to the carboxyl end of Y; and Z is aryl $C_1$–$C_6$ alkylamino or arylheterocyclyl $C_1$–$C_6$ alkylamino wherein an aryl group is linked to a heterocyclyl group; wherein aryl is a carbocyclic aryl; or a salt thereof.

18. A pharmaceutical composition comprising a pharmaceutically acceptable carrier and a compound of claim 17.

19. The compound of claim 1, which is of the formula:

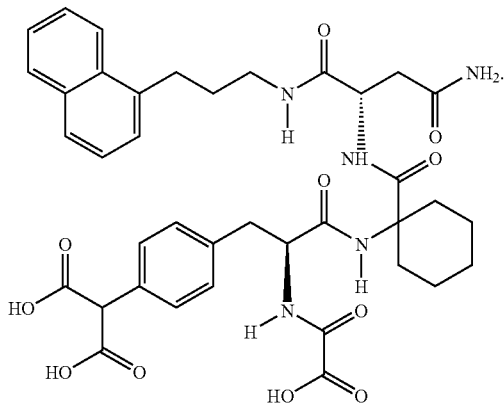

20. A pharmaceutical composition comprising a pharmaceutically acceptable carrier and the compound of claim 19.

21. A method for inhibiting an SH2 domain of a protein from binding with a phosphoprotein comprising contacting the SH2 domain with the compound of claim 19.

22. A method of inhibiting Grb2 signaling in a cancer cell in a patient comprising contacting the cell with the compound of claim 19.

23. A method of inhibiting MAP kinase activity in a mammal comprising administering to the mammal in need thereof the compound of claim 19.

24. The compound of claim 17, wherein n is 1–3.

25. The compound of claim 17, wherein Z is naphthylpropylamino.

26. The compound of claim 17, wherein the phenyl ring of Y includes a malonyl group.

27. The compound of claim 17, wherein the phenyl ring of Y includes a carboxymethyl group and a hydroxyl group.

28. The compound of claim 17, wherein said amino acid is selected from the group consisting of glycine, alanine, leucine, isoleucine, norleucine, cyclohexylalanine, 4-aminocyclohexylglycine, 4-acetylaminocyclohexylglycine, aspartic acid, asparagine, glutamic acid, and glutamine.

29. A method for treating breast cancer in a patient comprising administering to the patient an effective amount of the compound of claim 19.

30. A method of enhancing the therapeutic effect of a breast cancer treatment rendered to a mammal that has been afflicted with a breast cancer, comprising administering to the mammal the compound of claim 19 in conjunction with the treatment, wherein the treatment comprises chemotherapy, radiation therapy, or biological therapy.

31. A pharmaceutical composition comprising a pharmaceutically acceptable carrier and a compound of claim 2.

32. A pharmaceutical composition comprising a pharmaceutically acceptable carrier and a compound of claim 3.

33. A pharmaceutical composition comprising a pharmaceutically acceptable carrier and a compound of claim 4.

34. A pharmaceutical composition comprising a pharmaceutically acceptable carrier and a compound of claim 5.

35. A pharmaceutical composition comprising a pharmaceutically acceptable carrier and a compound of claim 6.

36. A pharmaceutical composition comprising a pharmaceutically acceptable carrier and a compound of claim 11.

37. A pharmaceutical composition comprising a pharmaceutically acceptable carrier and a compound of claim 13.

38. A pharmaceutically composition comprising a pharmaceutically acceptable carrier and a compound of claim 14.

39. A pharmaceutically composition comprising a pharmaceutically acceptable carrier and a compound of claim 15.

40. A method for inhibiting an SH2 domain of a protein from binding with a phosphoprotein comprising contacting the SH2 domain with the compound of claim 1.

41. A method for inhibiting an SH2 domain of a protein from binding with a phosphoprotein comprising contacting the SH2 domain with the compound of claim 2.

42. A method for inhibiting an SH2 domain of a protein from binding with a phosphoprotein comprising contacting the SH2 domain with the compound of claim 3.

43. A method of inhibiting Grb2 signaling in a cancer cell in a patient comprising contacting the cell with a compound of claim 1.

44. A method of inhibiting Grb2 signaling in a cancer cell in a patient comprising contacting the cell with a compound of claim 2.

45. A method of inhibiting Grb2 signaling in a cancer cell in a patient comprising contacting the cell with a compound of claim 3.

46. A method for inhibiting the growth of human breast cancer cells comprising contacting the cells with a compound of claim 1.

47. A method for inhibiting the growth of human breast cancer cells comprising contacting the cells with a compound of claim 2.

48. A method for inhibiting the growth of human breast cancer cells comprising contacting the cells with a compound of claim 3.

49. A method for inhibiting the growth of human breast cancer cells comprising contacting the cells with a compound of claim 17.

* * * * *